(12) United States Patent
Kelly

(10) Patent No.: US 9,573,094 B2
(45) Date of Patent: Feb. 21, 2017

(54) SYSTEM AND METHOD FOR TEMPERATURE CONTROL IN AN OXYGEN TRANSPORT MEMBRANE BASED REACTOR

(71) Applicant: Sean M. Kelly, Pittsford, NY (US)

(72) Inventor: Sean M. Kelly, Pittsford, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 221 days.

(21) Appl. No.: 14/509,406

(22) Filed: Oct. 8, 2014

(65) Prior Publication Data
US 2015/0099812 A1   Apr. 9, 2015

Related U.S. Application Data

(60) Provisional application No. 61/888,327, filed on Oct. 8, 2013.

(51) Int. Cl.
*B01D 53/46* (2006.01)
*C01B 13/02* (2006.01)
(Continued)

(52) U.S. Cl.
CPC .............. *B01D 53/46* (2013.01); *B01D 53/226* (2013.01); *B01J 8/009* (2013.01); *B01J 8/025* (2013.01);
(Continued)

(58) Field of Classification Search
CPC ........ B01J 8/062; B01J 19/2475; C01B 3/382; C01B 3/384; C01B 3/386; C01B 2203/00176; C01B 2203/00371; C01B 2203/00006; C01B 2203/0233; C01B 2203/0261
See application file for complete search history.

(56) References Cited

U.S. PATENT DOCUMENTS 2,593,507 A   4/1952   Wainer
2,692,760 A   10/1954  Flurschutz
(Continued)

FOREIGN PATENT DOCUMENTS

DE       10330859 A1    2/2004
DE    102004038435 A1   2/2006
(Continued)

OTHER PUBLICATIONS

Switzer et al., "Cost and Feasibility Study on the Praxair Advanced Boiler for the CO2 Capture Project's Refinery Scenario", Carbon Dioxide Capture for Deep Geologic Formations, vol. 1, D.C. Thomas and S.M. Benson (Eds.), Copyright 2005 Published by Elsevier Ltd., Chapter 32, pp. 561-579.
(Continued)

*Primary Examiner* — Matthew Merkling
(74) *Attorney, Agent, or Firm* — Ralph J. Mancini

(57) ABSTRACT

A system and method for temperature control in an oxygen transport membrane based reactor is provided. The system and method involves introducing a specific quantity of cooling air or trim air in between stages in a multistage oxygen transport membrane based reactor or furnace to maintain generally consistent surface temperatures of the oxygen transport membrane elements and associated reactors. The associated reactors may include reforming reactors, boilers or process gas heaters.

17 Claims, 24 Drawing Sheets

(51) Int. Cl.
*C01B 3/00* (2006.01)
*B01J 19/24* (2006.01)
*B01D 53/22* (2006.01)
*C07C 1/04* (2006.01)
*B01J 8/06* (2006.01)
*B01J 8/00* (2006.01)
*B01J 8/02* (2006.01)
*C01B 3/38* (2006.01)

(52) U.S. Cl.
CPC .......... *B01J 8/062* (2013.01); *B01J 8/065* (2013.01); *B01J 19/2475* (2013.01); *C01B 3/382* (2013.01); *C01B 3/384* (2013.01); *C01B 3/386* (2013.01); *C01B 13/0251* (2013.01); *C07C 1/041* (2013.01); *C07C 1/0485* (2013.01); *B01J 2208/00176* (2013.01); *B01J 2208/00371* (2013.01); *B01J 2219/00006* (2013.01); *B01J 2219/24* (2013.01); *C01B 2203/0233* (2013.01); *C01B 2203/0261* (2013.01); *C01B 2203/0805* (2013.01); *C01B 2203/0844* (2013.01); *C01B 2203/1241* (2013.01); *C01B 2203/148* (2013.01)

(56) References Cited

U.S. PATENT DOCUMENTS

| | | |
|---|---|---|
| 3,282,803 A | 11/1966 | Poepel et al. |
| 3,317,298 A | 5/1967 | Klomp et al. |
| 3,468,647 A | 9/1969 | Buyers et al. |
| 3,770,621 A | 11/1973 | Collins et al. |
| 3,861,723 A | 1/1975 | Kunz et al. |
| 3,868,817 A | 3/1975 | Marion et al. |
| 3,930,814 A | 1/1976 | Gessner |
| 3,976,451 A | 8/1976 | Blackmer et al. |
| 4,013,592 A | 3/1977 | Matsuoka et al. |
| 4,128,776 A | 12/1978 | Boquist et al. |
| 4,153,426 A | 5/1979 | Wintrell |
| 4,162,993 A | 7/1979 | Retalick |
| 4,175,153 A | 11/1979 | Dobo et al. |
| 4,183,539 A | 1/1980 | French et al. |
| 4,206,803 A | 6/1980 | Finnemore et al. |
| 4,261,167 A | 4/1981 | Paull et al. |
| 4,292,209 A | 9/1981 | Marchant et al. |
| 4,350,617 A | 9/1982 | Retalick et al. |
| 4,357,025 A | 11/1982 | Eckart |
| 4,365,021 A | 12/1982 | Pirooz |
| 4,373,575 A | 2/1983 | Hayes |
| 4,402,871 A | 9/1983 | Retalick |
| 4,609,383 A | 9/1986 | Bonaventura et al. |
| 4,631,238 A | 12/1986 | Ruka |
| 4,650,814 A | 3/1987 | Keller |
| 4,651,809 A | 3/1987 | Gollnick et al. |
| 4,720,969 A | 1/1988 | Jackman |
| 4,734,273 A | 3/1988 | Haskell |
| 4,749,632 A | 6/1988 | Flandermeyer et al. |
| 4,783,085 A | 11/1988 | Wicks et al. |
| 4,791,079 A | 12/1988 | Hazbun |
| 4,862,949 A | 9/1989 | Bell, III |
| 4,866,013 A | 9/1989 | Anseau et al. |
| 5,021,137 A | 6/1991 | Joshi et al. |
| 5,035,726 A | 7/1991 | Chen et al. |
| 5,061,297 A | 10/1991 | Krasberg |
| 5,143,751 A | 9/1992 | Richard et al. |
| 5,169,506 A | 12/1992 | Michaels |
| 5,169,811 A | 12/1992 | Cipollini et al. |
| 5,171,646 A | 12/1992 | Rohr |
| 5,185,301 A | 2/1993 | Li et al. |
| 5,205,990 A | 4/1993 | Lawless |
| 5,240,480 A | 8/1993 | Thorogood et al. |
| 5,259,444 A | 11/1993 | Wilson |
| 5,286,686 A | 2/1994 | Haig et al. |
| 5,298,469 A | 3/1994 | Haig et al. |
| 5,302,258 A | 4/1994 | Renlund et al. |
| 5,306,411 A | 4/1994 | Mazanec et al. |
| 5,342,705 A | 8/1994 | Minh et al. |
| 5,432,705 A | 8/1994 | Minh et al. |
| 5,356,730 A | 10/1994 | Minh et al. |
| 5,417,101 A | 5/1995 | Weich |
| 5,454,923 A | 10/1995 | Nachlas et al. |
| 5,478,444 A | 12/1995 | Liu et al. |
| 5,534,471 A | 7/1996 | Carolan et al. |
| 5,547,494 A | 8/1996 | Prasad et al. |
| 5,569,633 A | 10/1996 | Carolan et al. |
| 5,599,509 A | 2/1997 | Toyao et al. |
| 5,643,355 A | 7/1997 | Phillips et al. |
| 5,649,517 A | 7/1997 | Poola et al. |
| 5,707,911 A | 1/1998 | Rakhimov et al. |
| 5,750,279 A | 5/1998 | Carolan et al. |
| 5,804,155 A | 9/1998 | Farrauto et al. |
| 5,820,654 A | 10/1998 | Gottzman et al. |
| 5,820,655 A | 10/1998 | Gottzmann et al. |
| 5,837,125 A | 11/1998 | Prasad et al. |
| 5,855,762 A | 1/1999 | Phillips et al. |
| 5,864,576 A | 1/1999 | Nakatani et al. |
| 5,902,379 A | 5/1999 | Phillips et al. |
| 5,927,103 A | 7/1999 | Howard |
| 5,932,141 A | 8/1999 | Rostrop-Nielsen et al. |
| 5,944,874 A | 8/1999 | Prasad et al. |
| 5,964,922 A | 10/1999 | Keskar et al. |
| 5,975,130 A | 11/1999 | Ligh et al. |
| 5,980,840 A | 11/1999 | Kleefisch et al. |
| 6,010,614 A | 1/2000 | Keskar et al. |
| 6,035,662 A | 3/2000 | Howard et al. |
| 6,048,472 A | 4/2000 | Nataraj et al. |
| 6,051,125 A | 4/2000 | Pham et al. |
| 6,070,471 A | 6/2000 | Westphal et al. |
| 6,077,323 A | 6/2000 | Nataraj et al. |
| 6,110,979 A | 8/2000 | Nataraj et al. |
| 6,113,673 A | 9/2000 | Loutfy et al. |
| 6,114,400 A | 9/2000 | Nataraj et al. |
| 6,139,810 A * | 10/2000 | Gottzmann ............ B01J 8/009 422/201 |
| 6,153,163 A | 11/2000 | Prasad et al. |
| RE37,134 E | 4/2001 | Wilson |
| 6,214,066 B1 | 4/2001 | Nataraj et al. |
| 6,290,757 B1 | 9/2001 | Lawless |
| 6,293,084 B1 | 9/2001 | Drnevich et al. |
| 6,293,978 B2 | 9/2001 | Kleefisch et al. |
| 6,296,686 B1 | 10/2001 | Prasad et al. |
| 6,333,015 B1 | 12/2001 | Lewis |
| 6,352,624 B1 | 3/2002 | Crome et al. |
| 6,360,524 B1 | 3/2002 | Drnevich et al. |
| 6,368,491 B1 | 4/2002 | Cao et al. |
| 6,382,958 B1 | 5/2002 | Bool, III et al. |
| 6,394,043 B1 | 5/2002 | Bool, III et al. |
| 6,402,156 B1 | 6/2002 | Schutz et al. |
| 6,402,988 B1 | 6/2002 | Gottzmann et al. |
| 6,430,966 B1 | 8/2002 | Meinhardt et al. |
| 6,468,328 B2 | 10/2002 | Sircar et al. |
| 6,475,657 B1 | 11/2002 | Del Gallo et al. |
| 6,492,290 B1 | 12/2002 | Dyer et al. |
| 6,532,769 B1 | 3/2003 | Meinhardt et al. |
| 6,537,514 B1 | 3/2003 | Prasad et al. |
| 6,562,104 B2 | 5/2003 | Bool, III et al. |
| 6,592,731 B1 | 7/2003 | Lawless |
| 6,638,575 B1 | 10/2003 | Chen et al. |
| 6,641,626 B2 | 11/2003 | Van Calcar et al. |
| 6,652,626 B1 | 11/2003 | Plee |
| 6,681,589 B2 | 1/2004 | Brudnicki |
| 6,695,983 B2 | 2/2004 | Prasad et al. |
| 6,783,750 B2 | 8/2004 | Shah et al. |
| 6,786,952 B1 | 9/2004 | Risdal et al. |
| 6,811,904 B2 | 11/2004 | Gorte et al. |
| 6,846,511 B2 | 1/2005 | Visco et al. |
| 6,916,570 B2 | 7/2005 | Vaughey et al. |
| 7,077,133 B2 | 7/2006 | Yagi et al. |
| 7,125,528 B2 | 10/2006 | Besecker et al. |
| 7,153,559 B2 | 12/2006 | Ito et al. |
| 7,179,323 B2 | 2/2007 | Stein et al. |
| 7,229,537 B2 | 6/2007 | Chen et al. |
| 7,261,751 B2 | 8/2007 | Dutta et al. |
| 7,320,778 B2 | 1/2008 | Whittenberger |

(56) References Cited

U.S. PATENT DOCUMENTS

| | | |
|---|---|---|
| 7,351,488 B2 | 4/2008 | Visco et al. |
| 7,374,601 B2 | 5/2008 | Bonchonsky et al. |
| 7,396,442 B2 | 7/2008 | Bagby et al. |
| 7,427,368 B2 | 9/2008 | Drnevich |
| 7,470,811 B2 | 12/2008 | Thiebaut |
| 7,510,594 B2 | 3/2009 | Wynn et al. |
| 7,534,519 B2 | 5/2009 | Cable et al. |
| 7,556,676 B2 | 7/2009 | Nagabhushana et al. |
| 7,588,626 B2 | 9/2009 | Gopalan et al. |
| 7,658,788 B2 | 2/2010 | Holmes et al. |
| 7,786,180 B2 | 8/2010 | Fitzpatrick |
| 7,833,314 B2 | 11/2010 | Lane et al. |
| 7,846,236 B2 | 12/2010 | Del-Gallo et al. |
| 7,856,829 B2 | 12/2010 | Shah et al. |
| 7,871,579 B2 | 1/2011 | Tentarelli |
| 7,901,837 B2 | 3/2011 | Jacobson et al. |
| 7,906,079 B2 | 3/2011 | Whittenberger et al. |
| 7,968,208 B2 | 6/2011 | Hodgson |
| 8,070,922 B2 | 12/2011 | Nelson et al. |
| 8,128,988 B2 | 3/2012 | Yasumoto et al. |
| 8,196,387 B2 | 6/2012 | Shah et al. |
| 8,201,852 B2 | 6/2012 | Linhorst et al. |
| 8,262,755 B2 | 9/2012 | Repasky et al. |
| 8,323,378 B2 | 12/2012 | Swami et al. |
| 8,323,463 B2 | 12/2012 | Christie et al. |
| 8,349,214 B1 | 1/2013 | Kelly et al. |
| 8,419,827 B2 | 4/2013 | Repasky et al. |
| 8,435,332 B2 | 5/2013 | Christie et al. |
| 8,455,382 B2 | 6/2013 | Carolan et al. |
| 6,191,573 B1 | 11/2013 | Garing et al. |
| 8,658,328 B2 | 2/2014 | Suda et al. |
| 8,795,417 B2 | 8/2014 | Christie et al. |
| 8,894,944 B2 | 11/2014 | Larsen et al. |
| 2002/0073938 A1 | 6/2002 | Bool et al. |
| 2002/0078906 A1 | 6/2002 | Prasad et al. |
| 2002/0155061 A1 | 10/2002 | Prasad et al. |
| 2003/0039601 A1 | 2/2003 | Halvorson et al. |
| 2003/0039608 A1 | 2/2003 | Shah et al. |
| 2003/0054154 A1 | 3/2003 | Chen et al. |
| 2003/0068260 A1 | 4/2003 | Wellington |
| 2003/0230196 A1 | 12/2003 | Kim |
| 2004/0042944 A1 | 3/2004 | Sehlin et al. |
| 2004/0043272 A1 | 3/2004 | Gorte |
| 2004/0065541 A1 | 4/2004 | Sehlin |
| 2004/0089973 A1 | 5/2004 | Hoang |
| 2004/0221722 A1 | 11/2004 | Prasad et al. |
| 2005/0037299 A1 | 2/2005 | Gottzmann |
| 2005/0058871 A1 | 3/2005 | Li et al. |
| 2005/0061663 A1 | 3/2005 | Chen et al. |
| 2005/0137810 A1 | 6/2005 | Esposito, Jr. |
| 2005/0214612 A1 | 9/2005 | Visco et al. |
| 2005/0248098 A1 | 11/2005 | Sisk et al. |
| 2005/0263405 A1 | 12/2005 | Jacobson et al. |
| 2006/0029539 A1 | 2/2006 | Dutta et al. |
| 2006/0054301 A1 | 3/2006 | McRay et al. |
| 2006/0062707 A1 | 3/2006 | Crome et al. |
| 2006/0127656 A1 | 6/2006 | Gallo et al. |
| 2006/0127749 A1 | 6/2006 | Christie et al. |
| 2006/0191408 A1 | 8/2006 | Gopalan et al. |
| 2006/0236719 A1 | 10/2006 | Lane et al. |
| 2007/0004809 A1 | 1/2007 | Lattner et al. |
| 2007/0039466 A1 | 2/2007 | Nawata et al. |
| 2007/0041894 A1 | 2/2007 | Drnevich |
| 2007/0065687 A1 | 3/2007 | Kelly et al. |
| 2007/0082254 A1 | 4/2007 | Hiwatashi |
| 2007/0104793 A1 | 5/2007 | Akash |
| 2007/0137478 A1 | 6/2007 | Stein et al. |
| 2007/0158329 A1 | 7/2007 | Cao |
| 2007/0163889 A1 | 7/2007 | Kato et al. |
| 2007/0212271 A1 | 9/2007 | Kennedy |
| 2007/0289215 A1 | 12/2007 | Hemmings et al. |
| 2007/0292342 A1 | 12/2007 | Hemmings et al. |
| 2008/0000350 A1 | 1/2008 | Mundschau et al. |
| 2008/0000353 A1 | 1/2008 | Rarig et al. |
| 2008/0006532 A1 | 1/2008 | Mukundan et al. |
| 2008/0023338 A1 | 1/2008 | Stoots et al. |
| 2008/0029388 A1 | 2/2008 | Elangovan et al. |
| 2008/0047431 A1 | 2/2008 | Nagabhushana |
| 2008/0141672 A1 | 6/2008 | Shah |
| 2008/0168901 A1 | 7/2008 | Carolan et al. |
| 2008/0169449 A1 | 7/2008 | Mundschau |
| 2008/0226544 A1 | 9/2008 | Nakamura |
| 2008/0302013 A1 | 12/2008 | Repasky et al. |
| 2009/0001727 A1 | 1/2009 | De Koeijer et al. |
| 2009/0023050 A1 | 1/2009 | Finnerty et al. |
| 2009/0029040 A1 | 1/2009 | Christie et al. |
| 2009/0031895 A1 | 2/2009 | Del-Gallo et al. |
| 2009/0084035 A1 | 4/2009 | Wei |
| 2009/0107046 A1 | 4/2009 | Leininger |
| 2009/0120379 A1 | 5/2009 | Bozzuto et al. |
| 2009/0220837 A1 | 9/2009 | Osada |
| 2010/0015014 A1 | 1/2010 | Gopalan et al. |
| 2010/0074828 A1 | 3/2010 | Singh |
| 2010/0076280 A1 | 3/2010 | Bernstein et al. |
| 2010/0116133 A1 | 5/2010 | Reed et al. |
| 2010/0116680 A1 | 5/2010 | Reed et al. |
| 2010/0122552 A1 | 5/2010 | Schwartz |
| 2010/0143824 A1 | 6/2010 | Tucker et al. |
| 2010/0178219 A1 | 7/2010 | Verykios et al. |
| 2010/0178238 A1 | 7/2010 | Takamura et al. |
| 2010/0193104 A1 | 8/2010 | Ryu et al. |
| 2010/0200418 A1 | 8/2010 | Licht |
| 2010/0266466 A1 | 10/2010 | Froehlich et al. |
| 2010/0276119 A1 | 11/2010 | Doty |
| 2010/0313762 A1 | 12/2010 | Roeck et al. |
| 2011/0067405 A1 | 3/2011 | Armstrong et al. |
| 2011/0076213 A1 | 3/2011 | Carolan et al. |
| 2011/0111320 A1 | 5/2011 | Suda et al. |
| 2011/0120127 A1 | 5/2011 | Lippmann et al. |
| 2011/0132367 A1 | 6/2011 | Patel |
| 2011/0142722 A1 | 6/2011 | Hemmings et al. |
| 2011/0143255 A1 | 6/2011 | Jain et al. |
| 2011/0180399 A1 | 7/2011 | Christie et al. |
| 2011/0200520 A1 | 8/2011 | Ramkumar |
| 2011/0240924 A1 | 10/2011 | Repasky |
| 2011/0253551 A1 | 10/2011 | Lane et al. |
| 2012/0000360 A1 | 1/2012 | Richet et al. |
| 2012/0067060 A1 | 3/2012 | Greeff |
| 2012/0288439 A1 | 11/2012 | Sundaram et al. |
| 2012/0294783 A1 | 11/2012 | Palamara et al. |
| 2013/0009100 A1 | 1/2013 | Kelly et al. |
| 2013/0009102 A1 | 1/2013 | Kelly |
| 2013/0015405 A1* | 1/2013 | Quintero ............... B01D 71/025 252/373 |
| 2013/0072374 A1 | 3/2013 | Lane et al. |
| 2013/0072375 A1 | 3/2013 | Lane et al. |
| 2013/0156958 A1 | 6/2013 | Belov et al. |
| 2014/0044604 A1 | 2/2014 | Lane et al. |
| 2014/0056774 A1 | 2/2014 | Kelly et al. |
| 2014/0060643 A1 | 3/2014 | Martin et al. |
| 2014/0183866 A1 | 7/2014 | Kromer et al. |
| 2014/0206779 A1 | 7/2014 | Lackner |
| 2014/0319424 A1 | 10/2014 | Chakravarti et al. |
| 2014/0319427 A1 | 10/2014 | Chakravarti et al. |
| 2014/0323597 A1 | 10/2014 | Stuckert et al. |
| 2014/0323598 A1 | 10/2014 | Chakravarti et al. |
| 2014/0323599 A1 | 10/2014 | Chakravarti et al. |
| 2015/0098872 A1 | 4/2015 | Kelly et al. |

FOREIGN PATENT DOCUMENTS

| | | |
|---|---|---|
| EP | 0 926 096 A1 | 6/1999 |
| EP | 0 984 500 A2 | 3/2000 |
| EP | 0 989 093 A2 | 3/2000 |
| EP | 1 504 811 A1 | 2/2005 |
| EP | 1717420 A1 | 11/2006 |
| EP | 1743694 A1 | 1/2007 |
| EP | 2873451 A1 | 5/2015 |
| GB | 688657 | 3/1953 |
| GB | 689522 | 4/1953 |
| GB | 697377 | 9/1953 |
| GB | 713553 | 11/1954 |
| GB | 1199483 | 7/1970 |
| GB | 1 312 700 | 4/1973 |

(56) References Cited

FOREIGN PATENT DOCUMENTS

| | | |
|---|---|---|
| GB | 1348375 | 3/1974 |
| JP | 56-136605 | 10/1981 |
| WO | WO 9842636 | 10/1998 |
| WO | WO 0017418 | 3/2000 |
| WO | WO 0109059 A1 | 2/2001 |
| WO | WO 2007060141 | 5/2007 |
| WO | WO 2007086949 | 8/2007 |
| WO | WO 2008024405 | 2/2008 |
| WO | WO 2010052641 A1 | 5/2010 |
| WO | WO 2011083333 A1 | 7/2011 |
| WO | WO 2011121095 A2 | 10/2011 |
| WO | WO 2012118730 | 9/2012 |
| WO | WO 2013009560 A1 | 1/2013 |
| WO | WO 2013/062413 A1 | 5/2013 |
| WO | WO 2013089895 A1 | 6/2013 |
| WO | WO 2014074559 A1 | 5/2014 |
| WO | WO 2014077531 A1 | 5/2014 |
| WO | WO 2014/107707 A2 | 7/2014 |
| WO | WO 2014/176022 A1 | 10/2014 |

OTHER PUBLICATIONS

David Studer; Demonstration of a cylinder fill system based on solid electrolyte oxygen separator (SEOS) technology: Early field assessment at a USAF maintenance facility, (Air Products & Chemicals Inc.); AFRL-RH-BR-TR-2010-0046; Jun. 2010.
Zhu et al.; Development of Interconnect Materials for Solid Oxide Fuel Cells; Materials Science and Engineering A348, Apr. 23, 2002, pp. 227-243.
F. Bidrawn et al., "Efficient Reduction of CO2 in a Solid Oxide Electrolyzer" Electrochemical and Solid State Letters, vol. 11, No. 9, Jun. 20, 2008, pp. B167-B170, XP002644615, col. 1, 2.
Ebbesen et al., "Electrolysis of carbon dioxide in Solid Oxide Electrolysis Cells", Journal of Power Sources, Elsevier SA, CH, vol. 193, No. 1, Aug. 1, 2009, pp. 349-358, XP026150424, ISSN: 0378-7753, DOI: 10.1016/J. JPOWSOUR. 2009. 02. 093.
The U.S. Department of Energy, "Evaluation of Fossil Fuel Power Plants with CO2 Recovery", Final Report (Feb. 2002).
The U.S. Department of Energy—Office of Fossil energy and U.S. Department of Energy/NETL, "Evaluation of Innovative Fossil Fuel Power Plants with CO2 Removal", Interim Report (Dec. 2000).
Sylvain Deville; "Freeze-Casting of Porous Ceramics: A Review of Current Achievements and Issues"; Advanced Engineering Materials 2008, 10, No. 3, pp. 155-169.
Neville Holt, "Gasification Process Selection—Trade-offs and Ironies", Presented at the Gasification Technologies Conference 2004, Oct. 3-6, 2004 JW Marriott Hotel, Washington, DC, pp. 1-10.
Dyer et al., "Ion Transport Membrane Technology for Oxygen Separation and Syngas Production", Solid State Ionics 134 (2000) p. 21-33.
Andrea Montebelli et al., "Methods for the catalytic activation of metallic structured substrates", Catalysis Science & Technology, 2014, pp. 2846-2870.
Joseph J. Beaman, D.Sc.; "Oxygen Storage on Zeolites"; Prepared by USAF School of Aerospace Medicine, Human Systems Divisions (AFSC), Brooks Air Force Base, TX 78235-5301; USAFSAM-TR-88-26; AD-A209 352; pp. 1-77; Jan. 1989.
Radtke et al., "Renaissance of Gasification based on Cutting Edge Technologies", VGB PowerTech (2005), XP-001235150, pp. 106-115.
L. N. Protasova et al., "Review of Patent Publications from 1990 to 2010 on Catytic Coatings on Different Substrates, Including Microstructured Channels: Preparation, Deposition Techniques, Applications", Recent Patents on Chemical Engineering, 2012, pp. 28-44.
Zhimin Zhong, "Stoichiometric lanthanum chromite based ceramic interconnects with low sintering temperature", Solid State oflonics, North Holland Pub. Company, Amsterdam, NL, vol. 177 No. 7-8, Mar. 15, 2006, pp. 757-764, XP027895768,ISSN: 0167-2738.
Babcock & Wilcox, Steam 40, "Sulfur Dioxide Control" (1992), pp. 35-1-35-15.
M.F. Lu et al., Thermomechanical transport and anodic properties of perovskite-type (LaSr) CrFeO, Journal of Power Sources, Elsevier SA, CH, vol. 206, Jan. 15, 2012, pp. 59-69, XP028403091.
Okawa et al., Tri Design for a CO2 Recovery Power Plant by Burning Pulverized Coal in O2/CO2 , Energy Conyers. Mgmt., vol. 38, Supplement (1997) pp. S123-S127.
Ciacchi et al., "Tubular zirconia-yttria electrolyte membrane technology for oxygen separation", Solid State Ionics 152-153, 2002, pp. 763-768.
Friedemann Marschner et al., "Gas Production", Ullmann's Encyclopedia of Industrial Chemistry, Jun. 15, 2000, pp. 1-21, XP002253967.
Lee Rosen, Nick Degenstein; Minish Shah; Jamie Wilson; Sean Kelly; John Peck; and Max Christie; "Development of Oxygen Transport Membranes for Coal-Based Power Generation"; ScienceDirect (Available online at www.sciencedirect.com); Energy Procedia 4 (2011) pp. 750-755.

\* cited by examiner

SYSTEM AND METHOD FOR TEMPERATURE CONTROL IN AN OXYGEN TRANSPORT MEMBRANE BASED REACTOR

CROSS REFERENCE TO RELATED APPLICATIONS

This application claims the benefit of and priority to U.S. provisional patent application Ser. No. 61/888,327 filed Oct. 8, 2013, the disclosure of which is incorporated by reference herein.

STATEMENT OF GOVERNMENT RIGHTS

This invention was made with Government support under Cooperative Agreement No. DE-FC26-07NT43088, awarded by the United States Department of Energy. The Government has certain rights in this invention.

FIELD OF THE INVENTION

The present invention provides a system and method for temperature control in an oxygen transport membrane based reforming reactor configured to produce a synthesis gas from a hydrocarbon containing gaseous feed. More particularly, the present invention provides a method and apparatus to maintain generally consistent surface temperatures of the oxygen transport membrane elements and associated reforming reactors by introducing a specific quantity of cooling air or trim air in between stages in a multistage oxygen transport membrane based reforming reactor or furnace.

BACKGROUND

Synthesis gas containing hydrogen and carbon monoxide is produced for a variety of industrial applications, for example, the production of hydrogen, chemicals and synthetic fuel production. Conventionally, the synthesis gas is produced in a fired reformer in which natural gas and steam is reformed in nickel catalyst containing reformer tubes at high temperatures (e.g. 900° C. to 1000° C.) and moderate pressures (e.g 16 to 20 bar) to produce the synthesis gas. The endothermic heating requirements for steam methane reforming reactions occurring within the reformer tubes are provided by burners firing into the furnace that are fueled by part of the natural gas. In order to increase the hydrogen content of the synthesis gas produced by the steam methane reforming (SMR) process, the synthesis gas can be subjected to water-gas shift reactions to react residual steam in the synthesis gas with the carbon monoxide.

A well established alternative to steam methane reforming is the partial oxidation process (POx) whereby a limited amount of oxygen is allowed to burn with the natural gas feed creating steam and carbon dioxide at high temperatures and the high temperature steam and carbon dioxide are subjected to subsequent reforming reactions. A key shortcoming of both the SMR and POx processes is the significant amount of carbon emitted to the atmosphere as carbon dioxide gas in the low-pressure flue gas. In addition, producing synthesis gas by conventional SMR or POx processes are recognized to be a relatively expensive processes.

An attractive alternative process for producing synthesis gas is an oxygen-fired autothermal reformer (ATR) process that uses oxygen to partially oxidize natural gas internally in a reactor which retains nearly all the carbon in the high pressure synthesis gas, thus facilitating removal of carbon dioxide for carbon capture. However, the ATR process requires a separate air separation unit (ASU) to produce high purity, high-pressure oxygen, which adds complexity as well as capital and operating cost to the overall process.

As can be appreciated, the conventional methods of producing a synthesis gas such as SMR, POx or ATR systems are expensive and require complex installations. In order to overcome the complexity and expense of such installations it has been proposed to generate the synthesis gas within reactors that utilize an oxygen transport membrane to supply oxygen and thereby generate the heat necessary to support endothermic heating requirements of the steam methane reforming reactions. A typical oxygen transport membrane has a dense layer that, while being impervious to air or other oxygen containing gas, will transport oxygen ions when subjected to an elevated operational temperature and a difference in oxygen partial pressure across the membrane.

Examples of oxygen transport membrane based reforming reactors used in the production of synthesis gas can be found in U.S. Pat. Nos. 6,048,472; 6,110,979; 6,114,400; 6,296,686; 7,261,751; 8,262,755; and 8,419,827. The problem with all of these oxygen transport membrane based systems is that because such oxygen transport membranes need to operate at high temperatures of around 900° C. to 1100° C., preheating of the hydrocarbon feed to similarly high temperatures is often required. Where hydrocarbons such as methane and higher order hydrocarbons are subjected to such high temperatures, excessive carbon formation will occur in the feed stream, especially at high pressures and low steam to carbon ratios. The carbon formation problems are particularly severe in the above-identified prior art oxygen transport membrane based systems. A different approach to using an oxygen transport membrane based reforming reactor in the production of synthesis gas is disclosed in U.S. Pat. No. 8,349,214 and United States Patent Application Serial No. 2013/0009102 both of which disclose a reactively driven oxygen transport membrane based reforming system that uses hydrogen and carbon monoxide as part of the reactant gas feed which address many of the highlighted problems with the earlier oxygen transport membrane systems. Other problems that arise with the prior art oxygen transport membrane based reforming systems are the cost and complexity of the oxygen transport membrane modules and the lower than desired thermal coupling, durability, reliability and operating availability of such oxygen transport membrane based reforming systems. These problems are the primary reasons that oxygen transport membranes based reforming systems have not been successfully commercialized. Recent advances in oxygen transport membrane materials have addressed problems associated with oxygen flux, membrane degradation and creep life, but there is much work left to be done to achieve commercially viable oxygen transport membrane based reforming systems from a cost standpoint as well as from an operating reliability and availability standpoint.

Process designs that utilize thermally coupled separate oxygen transport membrane and catalytic reforming reactors have their own set of challenges. For example, oxygen transport membranes may be configured to perform several tasks such as separation of oxygen from air, reaction of permeated oxygen with a reactant stream to produce a water vapor containing reactant stream required to support endothermic reactions in the catalytic reforming reactor and transferring heat to drive the endothermic reactions in the catalytic reforming reactor to achieve desired production of synthesis gas. Heat to support endothermic reactions within catalytic reactors is mostly provided by radiant heat transfer of the heat released from combustion of permeated oxygen in the oxygen transport membrane reactor. At elevated temperatures the oxygen transport membranes are subjected to considerable mechanical stresses both during normal steady-state operation and transient operations such as start-up, shutdown, as well as, upset conditions, particularly at detrimental levels when temperatures or rate of temperature change may be outside acceptable ranges. Thus, inefficient transfer of exothermic heat released in the oxygen transport membrane reactors to the catalytic reforming reactors will lead to less efficient operation, higher capital cost and more complex system.

The need, therefore, continues to exist for a synthesis gas generation system or other oxygen transport membrane based reactor that has a high degree of thermal efficiency. The present invention addresses the aforementioned problems by providing a method and system for air temperature control in an oxygen transport membrane based reactor to maintain generally consistent surface temperatures of the oxygen transport membrane elements and associated reactors by introducing a specific quantity of cooling air or trim air in between stages in a multistage oxygen transport membrane based reactor.

SUMMARY OF THE INVENTION

The present invention in one or more aspects can be characterized as a method for temperature control in a multi-stage, reactively driven oxygen transport membrane based reactor comprising the steps of: (i) introducing a flow of a heated oxygen containing feed stream to the multi-stage reactively driven oxygen transport membrane based reactor, the heated oxygen containing feed stream having a temperature from about 800° C. to about 1000° C.; (ii) passing the heated oxygen containing feed stream across the surfaces of a plurality of oxygen transport membrane elements in a first stage of the multi-stage reactively driven oxygen transport membrane based reactor wherein the some oxygen is depleted from the heated oxygen containing feed stream to produce a first residual stream at a temperature at or above the heated oxygen containing feed stream temperature; (iii) passing the first residual stream through a first refractory air diffusion screen disposed proximate a distal end of the first stage of the multi-stage reactively driven oxygen transport membrane based reactor and configured to maintain an operating temperature in the first stage of the multi-stage reactively driven oxygen transport membrane based reactor and allow the first residual stream to pass therethrough; (iv) passing the first residual stream across the surfaces of a second plurality of oxygen transport membrane elements in a second stage of the multi-stage reactively driven oxygen transport membrane based reactor wherein the some oxygen is further depleted from the first residual stream to produce a second residual stream; (v) passing the second residual stream through a second refractory air diffusion screen disposed proximate a distal end of the second stage of the multi-stage reactively driven oxygen transport membrane based reactor and configured to maintain an operating temperature in the second stage of the multi-stage reactively driven oxygen transport membrane based reactor and allow the second residual stream to pass therethrough; and (vi) exhausting a stream containing some or all of the second residual stream from the multi-stage reactively driven oxygen transport membrane based reactor, wherein the operating temperature in the first stage and the operating temperature in the second stage are within about 25° C. of each other.

Alternatively, the invention may be characterized as a method for temperature control in a multi-stage reactively driven oxygen transport membrane based reactor comprising the steps of: (i) introducing a flow of a heated oxygen containing feed stream to the multi-stage reactively driven oxygen transport membrane based reactor, the heated oxygen containing feed stream having a temperature from about 800° C. to about 1000° C.; (ii) passing the heated oxygen containing feed stream across the surfaces of a plurality of oxygen transport membrane elements in a first stage of the multi-stage reactively driven oxygen transport membrane based reactor wherein the some oxygen is depleted from the heated oxygen containing feed stream to produce a first residual stream at a temperature at or above the heated oxygen containing feed stream temperature; (iii) passing the first residual stream through a first refractory air diffusion screen disposed proximate a distal end of the first stage of the multi-stage reactively driven oxygen transport membrane based reactor and configured to maintain an operating temperature in the first stage of the multi-stage reactively driven oxygen transport membrane based reactor and allow the first residual stream to pass therethrough; (iv) introducing a flow of supplemental cooling air to the first residual stream at a location downstream of the first refractory air diffusion screen within the multi-stage oxygen transport membrane based reactor; (v) mixing the flow of supplemental cooling air with the first residual stream to produce a mixed stream having a mixed stream temperature; (vi) passing the mixed stream across the surfaces of a second plurality of oxygen transport membrane elements in a second stage of the multi-stage reactively driven oxygen transport membrane based reactor wherein the some oxygen is depleted from the mixed stream to produce a second residual stream at a temperature above the mixed stream temperature; (vii) passing the second residual stream through a second refractory air diffusion screen disposed proximate a distal end of the second stage of the multi-stage reactively driven oxygen transport membrane based reactor and configured to maintain an operating temperature in the second stage of the multi-stage reactively driven oxygen transport membrane based reactor and allow the second residual stream to pass therethrough; and (viii) exhausting a stream containing some or all of the second residual stream from the multi-stage reactively driven oxygen transport membrane based reactor, wherein the operating temperature in the first stage and the operating temperature in the second stage are within about 25° C. of each other.

The invention may also be characterized as a multi stage reactively driven oxygen transport membrane based reactor comprising: (a) an air inlet configured to receive a heated oxygen containing feed stream at a temperature from about 800° C. to about 1000° C.; (b) a first plurality of oxygen transport membrane elements contained within a first stage of the multi-stage reactor and in fluid communication with the heated oxygen containing feed stream and configured to separate oxygen from the heated oxygen containing feed stream through oxygen ion transport when subjected to an elevated operational temperature and a reactively driven difference in oxygen partial pressure across the first plurality of oxygen transport membrane elements to produce an oxygen depleted first residual stream at a temperature above the heated oxygen containing feed stream; (c) a first refractory air diffusion screen disposed proximate a distal end of the first stage of the multi-stage reactively driven oxygen transport membrane based reactor and configured to maintain an operating temperature in the first stage of the multi-stage reactively driven oxygen transport membrane based reactor and allow the first residual stream to pass therethrough; (d) a second plurality of oxygen transport membrane elements contained within a second stage of the multi-stage reactor and disposed downstream of the first stage, the second plurality of oxygen transport membrane elements in fluid communication with the mixed stream and configured to separate oxygen from the mixed stream through oxygen ion transport when subjected to an elevated operational temperature and a reactively driven difference in oxygen partial pressure across the second plurality of oxygen transport membrane elements to produce an oxygen depleted second residual stream at a temperature above the heated oxygen containing feed stream; (e) a second refractory air diffusion screen disposed proximate a distal end of the second stage of the multi-stage reactively driven oxygen transport membrane based reactor and configured to maintain an operating temperature in the second stage of the multi-stage reactively driven oxygen transport membrane based reactor and allow the second residual stream to pass therethrough; and (f) an outlet disposed downstream of the second stage of the multi-stage reactively driven oxygen transport membrane based reactor and configured for exhausting a stream containing some or all of the oxygen depleted second residual stream from the multi-stage reactively driven oxygen transport membrane based reactor, wherein the operating temperature in the first stage and the operating temperature in the second stage are within about 25° C. of each other.

Finally, the invention may further be characterized as multi-stage reactively driven oxygen transport membrane based reactor comprising: (a) an air inlet configured to receive a heated oxygen containing feed stream at a temperature from about 800° C. to about 1000° C.; (b) a first plurality of oxygen transport membrane elements contained within a first stage of the multi-stage reactor and in fluid communication with the heated oxygen containing feed stream and configured to separate oxygen from the heated oxygen containing feed stream through oxygen ion transport when subjected to an elevated operational temperature and a reactively driven difference in oxygen partial pressure across the first plurality of oxygen transport membrane elements to produce an oxygen depleted first residual stream at a temperature above the heated oxygen containing feed stream; (c) a first refractory air diffusion screen disposed proximate a distal end of the first stage of the multi-stage reactively driven oxygen transport membrane based reactor and configured to maintain an operating temperature in the first stage of the multi-stage reactively driven oxygen transport membrane based reactor and allow the first residual stream to pass therethrough; (d) at least one cooling air injector disposed within the oxygen transport membrane based reactor downstream of the first stage and configured to introduce a flow of supplemental cooling air to the first residual stream and produce a mixed stream having a mixed stream temperature; (e) a second plurality of oxygen transport membrane elements contained within a second stage of the multi-stage reactor and disposed downstream of the first stage, the second plurality of oxygen transport membrane elements in fluid communication with the mixed stream and configured to separate oxygen from the mixed stream through oxygen ion transport when subjected to an elevated operational temperature and a reactively driven difference in oxygen partial pressure across the second plurality of oxygen transport membrane elements to produce an oxygen depleted second residual stream at a temperature above the heated oxygen containing feed stream; (f) a second refractory air diffusion screen disposed proximate a distal end of the second stage of the multi-stage reactively driven oxygen transport membrane based reactor and configured to maintain an operating temperature in the second stage of the multi-stage reactively driven oxygen transport membrane based reactor and allow the second residual stream to pass therethrough; and (g) an outlet disposed downstream of the second stage of the multi-stage reactively driven oxygen transport membrane based reactor and configured for exhausting a stream containing some or all of the oxygen depleted second residual stream from the multi-stage reactively driven oxygen transport membrane based reactor, wherein the operating temperature in the first stage and the operating temperature in the second stage are within about 25° C. of each other.

In some embodiments, the multi-stage reactively driven oxygen transport membrane based reactor is a reactively driven oxygen transport membrane based reforming reactor. In other embodiments, the multi-stage reactively driven oxygen transport membrane based reactor is a reactively driven oxygen transport membrane boiler or a reactively driven oxygen transport membrane based process gas heater.

In some embodiments, the addition of supplemental cooling air is introduced at multiple locations within the multi-stage reactively driven oxygen transport membrane based reactor, including, for example upstream of the first stage, between the first stage and the second stage, between the second and third stages, between any successive stages, or even downstream of the last stage prior to the outlet.

In the various embodiments of the presently claimed systems and methods, the air temperature control and thermal management of multi-stage, reactively driven oxygen transport membrane based reactor may be further advantageously achieved by maintaining the temperature of the first residual stream and the temperature of the second residual stream within about 25° C. of each other. Alternatively, the addition or mixing of supplemental cooling air allows for maintaining the exhausted stream, the first residual stream, and/or the second residual stream at temperatures not greater than about 50° C. above the heated oxygen containing feed stream and/or the mixed stream temperatures

BRIEF DESCRIPTION OF THE DRAWINGS

The above and other aspects, features, and advantages of the present invention will be more apparent from the following, more detailed description thereof, presented in conjunction with the following drawings, in which.

DETAILED DESCRIPTION

Broadly speaking, the present invention may be characterized as an improved oxygen transport membrane based reforming reactor for producing synthesis gas. The improved reactor and system provides enhanced thermal coupling of oxygen transport membrane tubes and catalytic containing reforming tubes as well as improved manufacturability, maintainability and operability compared to previously disclosed oxygen transport membrane based reforming systems and reactors. In an alternate embodiment, the improved reactor and system is an oxygen transport membrane boiler or process gas heater that provides enhanced thermal coupling of oxygen transport membrane tubes with steam tubes or process gas heating tubes. Each of these embodiments are discussed in the paragraphs that follow.

Reactively Driven Oxygen Transport Membrane Based Reforming System

Figure 1:
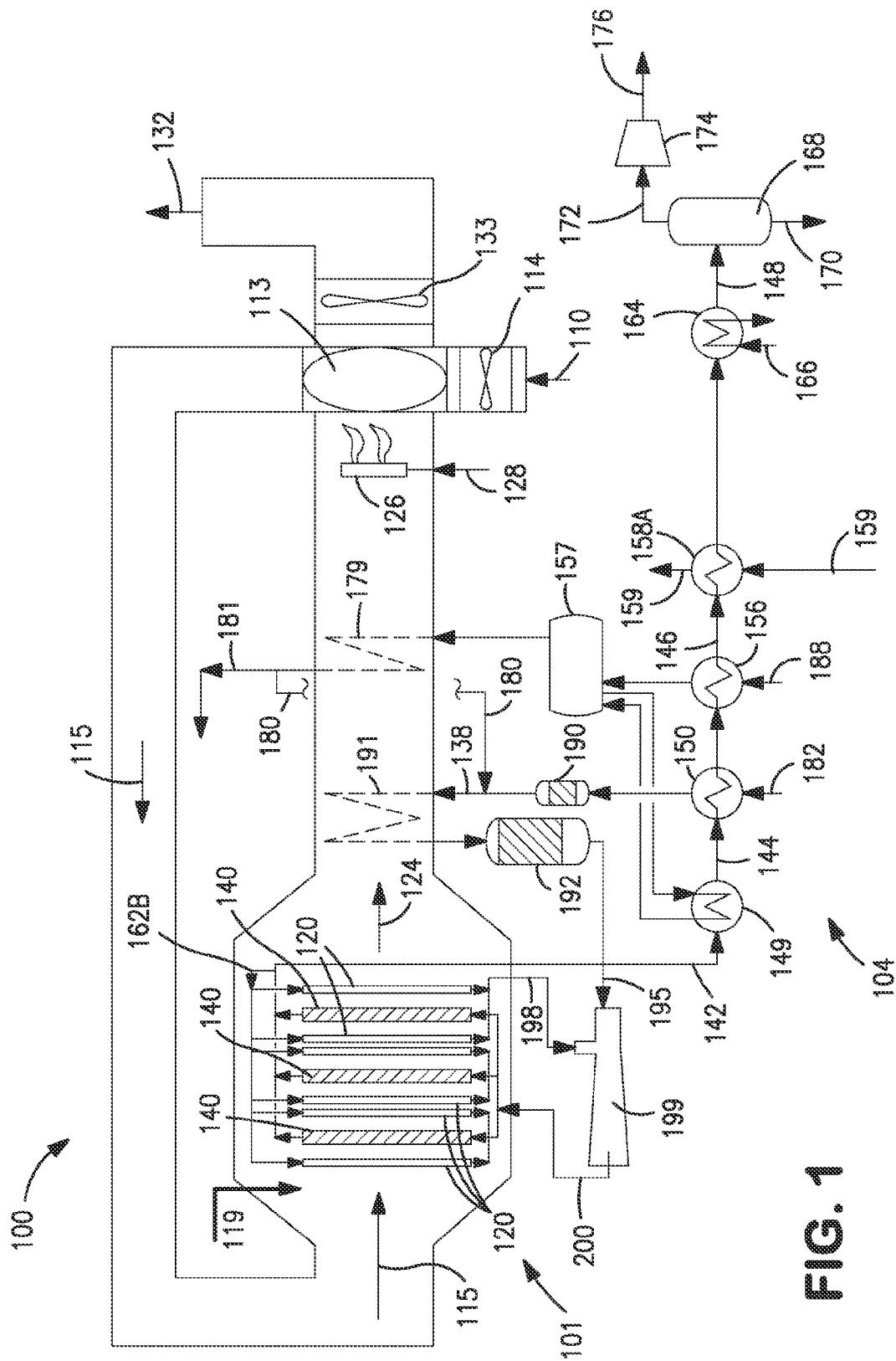
FIG. 1 shows a schematic illustrations of an embodiment of the present oxygen transport membrane system.
Figure 3A:
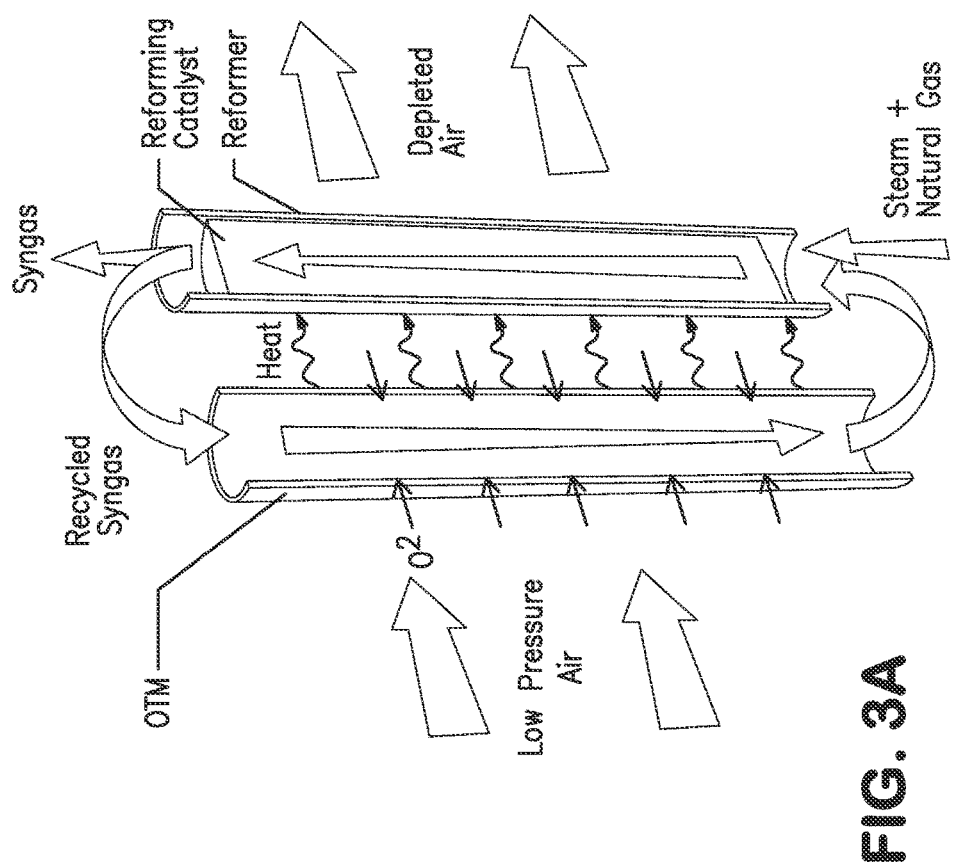
FIGS. 3A, 3B, 3C, and 3D schematic illustrations of four alternate embodiments of the oxygen transport membrane technology and reactor configurations.

For purposes of describing the general operation of the reactively driven oxygen transport membrane based reforming reactor and system, FIG. 1 and FIG. 3A show schematic illustrations of the system as well as the underlying oxygen transport membrane technology and reactor configuration. As seen therein, an oxygen containing stream 110, such as air, is introduced to the system 100 by means of a blower or fan 114 into a heat exchanger 113 for purposes of preheating the oxygen containing stream 110. Heat exchanger 113 is preferably a high efficiency, cyclic or continuously rotating regenerator disposed in operative association with the oxygen containing stream 110 and the heated retentate stream 124. The heated and oxygen depleted retentate stream 124 can optionally be introduced into a duct burner region containing duct burner 126 and used to support combustion of a supplemental fuel stream 128 to produce supplemental heat introduced into the continuously rotating regenerator 113 to preheat the oxygen containing stream 110. Exhaust stream 132 from heat exchanger 113 is discharged.

The heated oxygen containing stream 115 is then directed via the intake duct to the oxygen transport membrane elements 120 incorporated into the oxygen transport membrane based reforming reactor 101. Each of the oxygen transport membrane elements 120 are preferably configured as a multilayered ceramic tube capable of conducting oxygen ions at an elevated operational temperature, wherein the retentate side of the oxygen transport membrane elements 120 is the exterior surface of the ceramic tubes exposed to the oxygen containing stream and the permeate side is the interior surface of the ceramic tubes. Although only six oxygen transport membrane elements 120 are illustrated in close proximity to three catalytic reforming tubes 140, as would occur to those skilled in the art, there could be many of such oxygen transport membrane elements and many catalytic reforming tubes in each oxygen transport membrane assembly. Likewise, there would be multiple oxygen transport membrane assemblies used in an industrial application of the oxygen transport membrane based reforming reactor 101. In addition, a stream of cooling air 119 or trim air may be injected and mixed with the heated air stream 115 as a means to provide air temperature control within the oxygen transport membrane based reforming reactor 101, particularly in applications where multiple reactors are arranged in series in a oxygen transport membrane furnace, as described in more detail below.

A hydrogen containing stream is also introduced into the permeate side of the oxygen transport membrane elements 120 and is oxidized though reaction with the permeated oxygen to produce a reaction product stream 198 and heat. The hydrogen containing stream is preferably a recycled portion of the produced synthesis gas 163. As a result of separation of oxygen and the reaction (i.e. combustion) occurring at the permeate side of oxygen transport membrane elements 120, a heated, oxygen depleted retentate stream 124 is also formed.

The hydrogen containing stream is preferably a portion of the heated synthesis gas stream exiting the catalyst reforming tubes. A portion of heated synthesis gas, preferably between 25% and 50%, is recycled to the permeate side of the oxygen transport membrane tubes 120 to react with the oxygen permeate stream to generate the heated reaction product stream and radiant heat. The temperature of the hot synthesis recycled gas is preferably above 1500° F. so as to avoid problems associated with metal dusting corrosion.

The hot synthesis gas stream 162 is driven or pulled to the permeate side of the oxygen transport membrane tubes or elements 120 by means of an ejector, eductor or venturi based device 199 operatively coupled to the permeate side of the oxygen transport membrane elements 120. By suctioning the streams at the permeate side of the oxygen transport membrane elements 120 into the ejector, eductor or venturi based device 199 with a motive fluid comprising the pre-reformed reformer feed stream 195, the reaction product stream 198 mixes with the pre-reformed reformer feed stream 195 to produce the combined feed stream 200, preferably having a steam to carbon ratio between about 1.6 and 3.0 and a temperature between about 1000° F. and 1400° F. Essentially, device 199 moves the lower pressure hot synthesis gas recycle stream 162 to the higher pressure combined feed stream 200.

The reaction of the hydrogen containing stream or recycled synthesis gas stream 163 at the permeate side of the oxygen transport membrane element 120 produces heat. Radiation of this heat together with the convective heat transfer provided by heated retentate stream 124 heats the catalytic reactor tubes 140 to supply the endothermic heating requirements of the steam methane reforming occurring in catalytic reactor tubes 140. As the heated retentate stream 124 exits the oxygen transport membrane based reforming reactor 101, it also heats a reformer feed stream 138 to a temperature between about 900° F. and 1200° F. via indirect heat transfer using one or more coils 191 disposed in the retentate duct such that the oxygen depleted retentate stream 124 heats the feed streams passing through the coils 191. Also note that any superheated steam not added or used in the natural gas feed 182 may be exported steam 181 that can be used for power generation.

The hydrocarbon containing feed stream 182 to be reformed is preferably natural gas. Depending on the supply pressure, the natural gas is compressed or let down to the desired pressure via a compressor or valve arrangement (not shown) and then preheated in heat exchanger 150 that serves as a fuel preheater. Also, since the natural gas typically contains unacceptably high level of sulfur species, the natural gas feed stream 182 undergoes a sulfur removal process such as hydrotreating, via device 190, to reduce the sulfur species to $H_2S$, which is subsequently removed in a guard bed using material like ZnO and/or CuO. The hydrotreating step also saturates any alkenes present in the hydrocarbon containing feed stream. Further, since natural gas generally contains higher hydrocarbons that will break down at high temperatures to form unwanted carbon deposits that adversely impact the reforming process, the natural gas feed stream 182 is preferably pre-reformed in an adiabatic pre-reformer 192, which converts higher hydrocarbons to methane, hydrogen, carbon monoxide, and carbon dioxide. Pre-reformers are typically catalyst-based systems. Although not shown, this pre-reformed reformer feed stream 195 may be further heated via indirect heat exchange with the heated retentate stream 124. Also contemplated, but not shown, is an embodiment where the pre-reformer may comprise a heated pre-reformer that is thermally coupled with the heated retentate stream 124.

In the illustrated system, the above-described heated reaction product stream 198 is combined with the heated pre-reformed reformer feed stream 195 to produce a combined feed stream 200 that contains steam and hydrocarbons. This combined feed stream is introduced into the catalytic reactor tubes 140 where the combined feed stream 200 is subjected to steam methane reforming to produce a synthesis gas stream 142. The temperature of the combined feed stream 200 is between about 1000° F. and 1400° F., and more preferably between about 1100° F. and 1400° F. Steam 180 may also be added to the combined feed stream 200, the natural gas feed stream 182, or the preheated pre-reformed reformer feed stream 195, as required, to adjust the temperature of stream 200 as well as the steam to carbon ratio of stream 200 to between about 1.6 and 3.0, and more preferably to steam to carbon ratio between about 2.0 and 2.8. The steam is preferably superheated steam 180 between about 300 psia and 1200 psia and between about 600° F. and 1100° F. and heated by means of indirect heat exchange with the heated retentate stream 124 using steam coils 179 disposed in the retentate duct. The superheated steam 180 is preferably added to the hydrocarbon containing feed stream 182 upstream of the pre-reformer 192 to adjust the steam to carbon ratio and final temperature of the combined feed stream 200. Also, to reduce the methane slip and optimize the economic performance of the oxygen transport membrane based reforming reactor, the oxygen transport membrane reactor 101 should preferably be maintained at an exit pressure of less than or equal to about 500 psia.

The synthesis gas stream 142 produced by the oxygen transport membrane based reforming reactor 101 generally contains hydrogen, carbon monoxide, steam and carbon dioxide other constituents such as possible methane slip. Heat exchange section 104 is designed to cool the produced synthesis gas stream 142. The heat exchange section 104 is also designed such that in cooling the synthesis gas stream 142, various feed streams are preheated and process steam is also generated.

The initial cooling of synthesis gas stream 142 is accomplished with steam generation in a process gas boiler (PG boiler) 149 coupled to steam drum 157 and designed to reduce the temperature of the cooled synthesis gas 144 to about 760° F. or less. As illustrated in FIG. 1, the initially cooled synthesis gas stream 144 is successively further cooled in a heat exchange network that includes hydrocarbon feed preheater 150, economizer 156, feed water heaters 158, synthesis gas cooler 161 and water cooled heat exchanger 164. The initially cooled synthesis gas stream 144 is directed to the fuel preheater 150 to heat the natural gas feed stream 182 and then is directed to the economizer 156 to heat boiler feed water 188. The boiler feed water stream 188 is preferably pumped using a feed water pump (not shown), heated in economizer 156 and sent to steam drum 157.

The cooled synthesis gas stream 146 is further cooled in a series of steps including a feed water heater 158, used to heat feed water stream 159, followed by a synthesis gas cooler 161 and a subsequent water cooled heat exchanger 164 cooled via a separate cooling water stream 166. The heated feed water 159 is directed to a de-aerator (not shown) that provides boiler feed water 188. The resulting fully cooled synthesis gas stream 148 is then introduced into a knock-out drum 168 from which a condensate stream 170 is drained to produce a fully cooled synthesis gas stream 172. The fully cooled synthesis gas stream 172 may be compressed in a synthesis gas compressor 174 to produce a synthesis gas product 176.

The produced synthesis gas should have a module of between about 1.5 and 2.2. In addition, such produced synthesis gas stream ideally has a methane slip of less than about 4.5 percent by volume where the exit pressure of the oxygen transport membrane based reforming reactor is 500 psia or less, and more preferably, a methane slip of less than about 2.5 percent by volume where the exit pressure of the reforming reactor is 200 psia or less.

Figure 2:
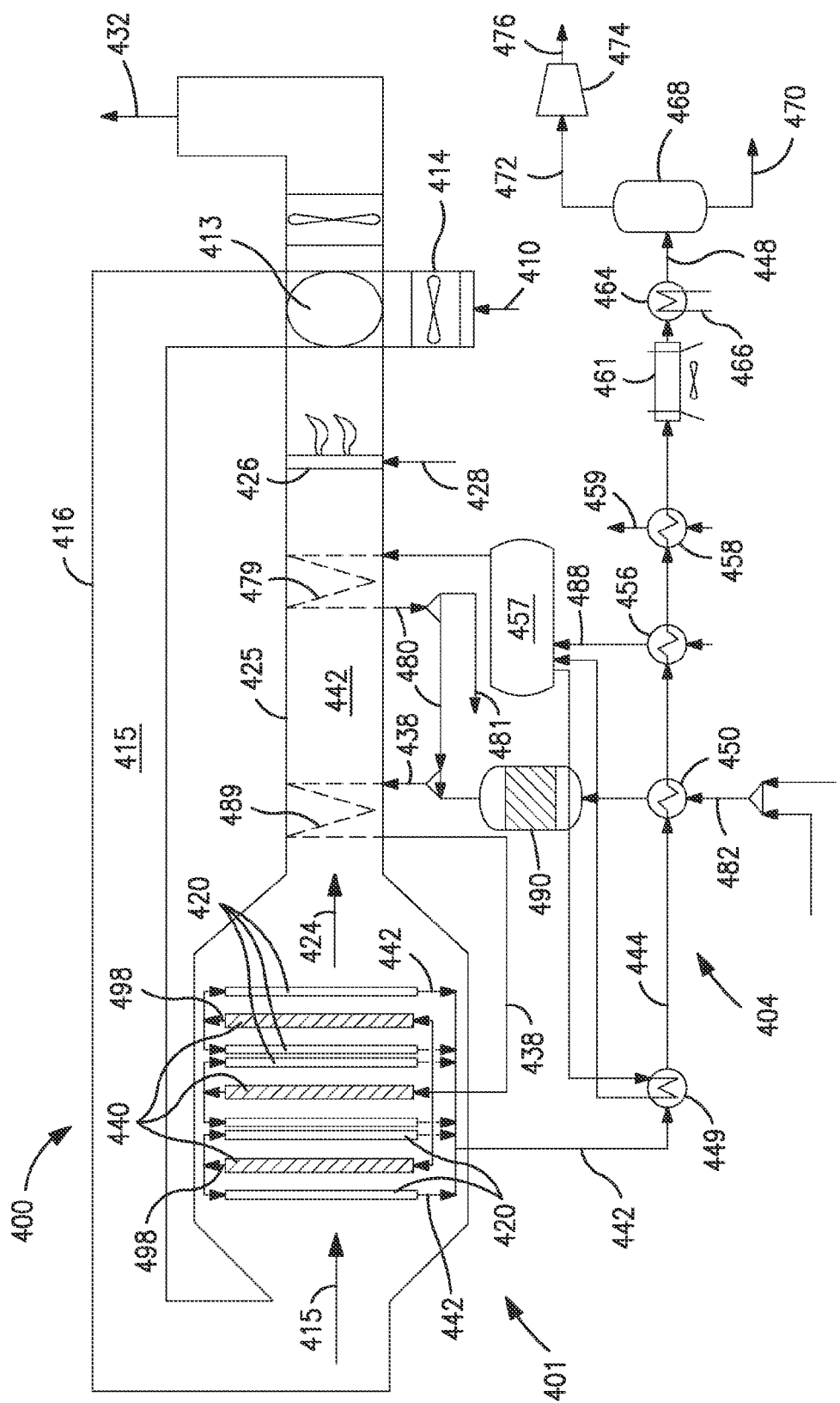
FIG. 2 shows a schematic illustrations of an alternate embodiment of the present oxygen transport membrane system.
Figure 3B:
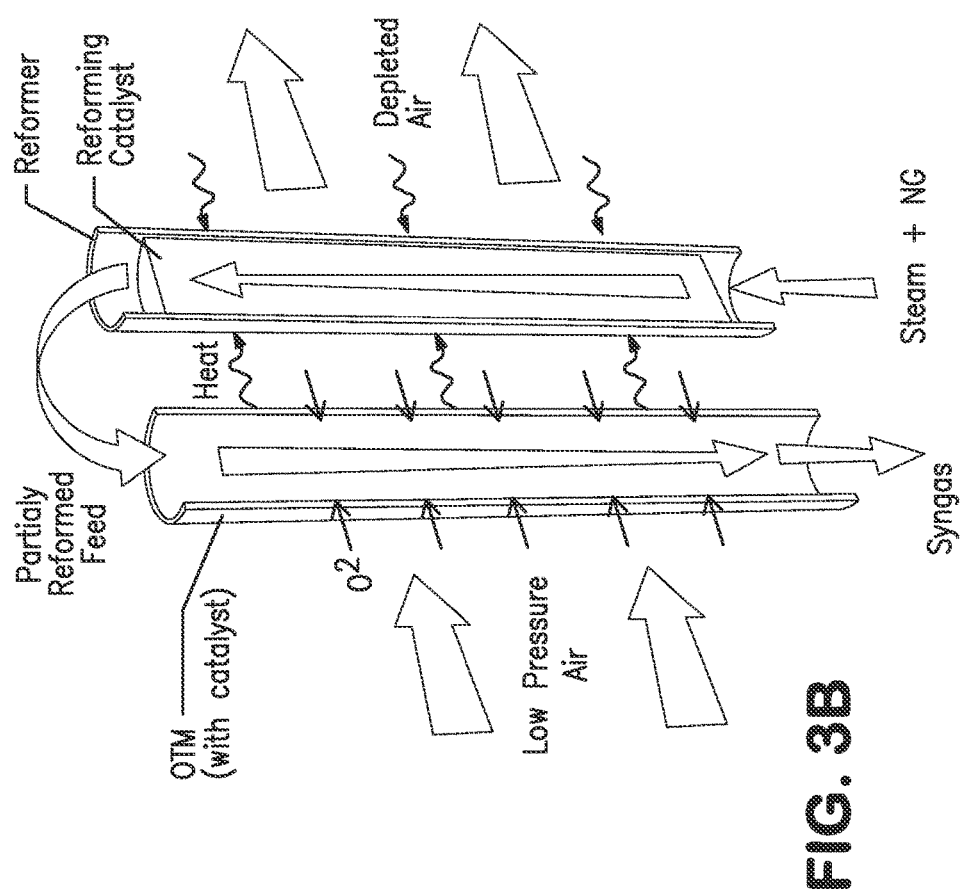

With reference to FIGS. 2 and 3B, an alternate embodiment of the oxygen transport membrane based reforming system is shown as an oxygen transport membrane based combined reforming system 401 that preferably comprises two reactors, namely a reforming reactor and oxygen transport membrane reactor. The reforming reactor consists of a plurality of catalyst containing reforming tubes 440 in which primary reforming of a natural gas feed occurs and the oxygen transport membrane reactor consists of a plurality of catalyst containing oxygen transport membrane tubes 420 where the secondary reforming occurs. FIG. 3 depicts a mock-up of the general arrangement of the two reactors and the flows associated therewith. FIG. 4, on the other hand, shows a schematic illustration of the oxygen transport membrane based combined reforming system 401. Although only six secondary reforming oxygen transport membrane tubes 420 are illustrated in FIG. 2 in close proximity to three primary reforming tubes 440, as would occur to those skilled in the art, there could be many of such secondary reforming oxygen transport membrane tubes and many primary reforming tubes in each oxygen transport membrane sub-system. Likewise, there would be multiple oxygen transport membrane sub-systems used in industrial applications of the oxygen transport membrane based combined reforming system 401.

As depicted in the FIG. 2, a heated oxygen containing stream 415 is directed via an intake duct 416 to a plurality of secondary reforming oxygen transport membrane tubes 420 incorporated into the oxygen transport membrane system 401. The secondary reforming oxygen transport membrane tubes 420 are preferably configured as multi-layered ceramic tubes capable of conducting oxygen ions at an elevated operational temperature, wherein the oxidant side or retentate side of the secondary reforming oxygen transport membrane tubes 420 is the exterior surface of the ceramic tubes exposed to the heated oxygen containing stream 415 and the reactant side or permeate side is the interior surface of the ceramic tubes. Within each of the secondary reforming oxygen transport membrane tubes 420 are one or more catalysts that facilitate partial oxidation and reforming of the natural gas.

A hydrocarbon containing feed stream 492, preferably natural gas, to be reformed is typically mixed with a small amount of hydrogen or hydrogen-rich gas 493 and preheated to around 370° C. in heat exchanger 450 that serves as a feed pre-heater. Since natural gas typically contains unacceptably high level of sulfur species, a small amount of hydrogen is typically added to facilitate desulfurization. The heated feed stream 482 undergoes a sulfur removal process via device 490 such as hydro-treating to reduce the sulfur species to $H_2S$, which is subsequently removed in a guard bed using material like ZnO and/or CuO. The hydro-treating step also saturates any alkenes present in the hydrocarbon containing feed stream. Although not shown, the heated feed stream 482 may also undergo a pre-reforming step in, for example, an adiabatic pre-reformer which converts higher hydrocarbons to methane, hydrogen, carbon monoxide, and carbon dioxide or a heated pre-reforming step. In the case of heated pre-reforming, it is contemplated that the catalyst based pre-reformer be thermally coupled with the oxygen transport membrane reforming system.

Superheated steam 480 is added to the pre-treated natural gas and hydrogen feed stream, as required, to produce a mixed feed stream 438 with a steam to carbon ratio preferably between about 1.0 and 2.5, and more preferably between about 1.2 and 2.2. The superheated steam 480 is preferably between about 15 bar and 80 bar and between about 300° C. and 600° C. and generated by means of indirect heat exchange with the heated retentate stream 424 using steam coils 479 disposed in the retentate duct 425. Any superheated steam 480 not added or used in the natural gas and hydrogen feed 482 is exported steam 481 used for power generation. The mixed feed stream 438 is heated, by means of indirect heat exchange with the heated retentate stream using coils 489 disposed in the retentate duct 425, to preferably between about 450° C. and 650° C., and more preferably between about 500° C. and 600° C.

The heated mixed feed stream 438 is then sent to the reforming tubes 440, which contain a reforming catalyst. The temperature of the partially reformed hydrogen-rich synthesis gas 498 leaving the reforming tubes 440 is typically designed to be between 650° C. and 850° C. This synthesis gas is then fed to the oxygen transport membrane tubes 420 filled with or containing a reforming catalyst. Oxygen from the heated intake air permeates through the oxygen transport membrane tubes 420 and facilitates reaction of a portion of the partially reformed synthesis gas 498. A portion of the energy or heat generated by this reaction is used for in-situ secondary reforming of the residual methane in the partially reformed synthesis gas 498. The rest of the energy or heat is transferred by radiation to the reforming tubes 440 to drive the primary reforming reactions and by convection to the oxygen-depleted stream 424. The synthesis gas 442 leaving the oxygen transport membrane tubes 420, which essentially function as a secondary reformer, is at a temperature between about 900° C. and 1050° C.

The endothermic heating requirements of the reforming process occurring in the primary reforming tubes 440 is supplied through radiation of some of the heat from the secondary reforming oxygen transport membrane tubes 420 together with the convective heat transfer provided by heated retentate stream 424. In addition, as the heated, oxygen depleted retentate stream 424 exits the oxygen transport membrane based reforming system 401, it also heats the mixed feed stream 438 to a temperature between about 450° C. and 650° C. via indirect heat transfer using one or more coils 489 disposed in the retentate stream duct 425.

The rest of the alternate embodiment of the oxygen transport membrane reforming subsystem shown in FIG. 3 is in many respects similar to the embodiment shown in FIG. 1. For example, an oxygen containing stream 410 is introduced to the system by means of a forced draft (FD) fan 414 into a heat exchanger 413 for purposes of preheating the oxygen containing feed stream 410 to a temperature in the range of about 500° C. to 1050° C.

The oxygen depleted air leaves the oxygen transport membrane reforming tubes as a heated retentate stream 424 at a slightly higher temperature than the heated air feed stream 415. Any temperature increase, typically <50° C., is attributable to the portion of energy generated by oxidizing reaction of hydrogen and carbon monoxide in the oxygen transport membrane tubes and transferred by convection to the air stream, offset by the introduction of supplemental feed air, as described in more detail below. The heated, oxygen depleted retentate stream 424 is first used to heat the mixed feed stream to a temperature between about 450° C. and 650° C., and more preferably to a temperature between 500° C. and 600° C., and may also be used to further heat steam to superheated steam.

The temperature of this oxygen depleted retentate stream 424 preferably needs to be then increased back to a temperature between about 1050° C. and 1200° C. prior to being directed to the ceramic heat exchanger or regenerator 413. This increase in temperature of the retentate stream 424 is preferably accomplished by use of a duct burner 426, which facilitates combustion of a supplemental fuel stream 428 using some of the residual oxygen in the retentate stream 424. It is conceivable that the mixed feed heater and steam superheater could alternatively be located in a separate fired heater (not shown). In that case, the fuel requirements of the duct burner 426 will be substantially less. The resulting cold retentate stream exiting the ceramic heat exchanger, typically containing less than 5% oxygen, leaves the oxygen transport membrane based reforming system 401 system as exhaust gas 432 at a temperature of around 150° C.

Turning again to FIG. 3, the synthesis gas stream 442 produced by the oxygen transport membrane based reforming system 401 generally contains hydrogen, carbon monoxide, unconverted methane, steam, carbon dioxide and other constituents. A significant portion of the sensible heat from the synthesis gas stream 442 can be recovered using a heat exchange section or recovery train 404. Heat exchange section 404 is designed to cool the produced synthesis gas stream 442 exiting the oxygen transport membrane based reforming system 401. While cooling the synthesis gas stream 442, process steam is generated, hydrocarbon feed stream is preheated, and boiler feed water is heated.

To minimize metal dusting issues, the hot synthesis gas 442 is directly cooled to about 400° C. or less in a Process Gas (PG) Boiler 449. The initially cooled synthesis gas stream 444 is then used to preheat the mixture of natural gas and hydrogen feed stream 482 in a fuel pre-heater 450 and subsequently to pre-heat boiler feed water 488 in the economizer 456 and to heat the feed water stream 459. In the illustrated embodiment, the boiler feed water stream 488 is preferably pumped using a feed water pump (not shown), heated in economizer 456 and sent to steam drum 457 while the heated feed water 459 is sent to a de-aerator (not shown) that provides boiler feed water 488. Synthesis gas leaving the feedwater heater 458 is preferably around 150° C. It is cooled down to 40° C. using a fin-fan cooler 461 and a synthesis gas cooler 464 fed by cooling water 466. The cooled synthesis gas 448 then enters a knock-out drum 468 where water is removed from the bottoms as process condensate stream 470 which, although not shown, is recycled for use as feedwater, and the cooled synthesis gas 472 is recovered overhead.

The cooled synthesis gas stream 472 is optionally compressed in a synthesis gas compressor 474 to produce a synthesis gas product 476. Depending on the operating pressure of the oxygen transport membrane based reforming system, pressure of the recovered synthesis gas is preferably in the range of about 150 psia and 500 psia and more preferably in the range of 175 psia and 400 psia. The module of the synthesis gas produced in the described embodiment is typically less than about 2.0 and often less than about 1.9, whereas for some synthesis gas applications such as methanol synthesis, the desired module of the synthesis gas is preferably in the range of about 2.0 to 2.2. Use of an adiabatic pre-reformer upfront of the OTM reactor can increase the module by about 0.05 to 0.1 relative to the configuration without a pre-reformer. With a heated pre-reformer, it becomes possible to achieve higher modules, preferably greater than 2 and definitely greater than 1.9. The exact module value depends on the reactor operating temperature.

Oxygen Transport Membrane Reforming Module

From the foregoing discussion, it can be readily appreciated that a reactively driven oxygen transport membrane assembly or module can be constructed or comprised of: (i) a plurality of tubular ceramic oxygen transport membranes configured to transport oxygen ions from an oxygen containing stream present at the outside surface or retentate side of the tubular ceramic oxygen transport membranes to the interior surface or permeate side of the tubular ceramic oxygen transport membranes; (ii) a plurality of catalyst containing reformer tubes disposed adjacent or juxtaposed relationship with the ceramic oxygen transport membrane tubes and configured to produce synthesis gas from the hydrocarbon feed in the presence of a reforming catalyst and radiant heat generated from the tubular ceramic oxygen transport membranes; (iii) a first manifold with associated seals to allow for a flow of a hydrocarbon feed gas and steam through the catalyst containing reformer tubes to produce a synthesis gas; (iv) a second manifold with associated seals to allow for the flow of a hydrogen containing gas such as synthesis gas and steam through the tubular ceramic oxygen transport membranes; (v) a recycle circuit to provide a portion of the synthesis gas produced in the catalyst containing reformer tubes to the tubular ceramic oxygen transport membranes; (vi) an inlet circuit configured to provide steam and supply the hydrocarbon feed to the assembly or module and the plurality of catalyst containing reformer tubes contained therein; (vii) an outlet circuit with exit manifold configured to withdraw the synthesis gas produced in the plurality of catalyst containing reformer tubes from the assembly or module; and (viii) an air staging system configured to supply the required volume of heated intake air and supplemental cooling air to the oxygen transport membrane based reforming reactor or furnace as well as provide the air temperature control in the oxygen transport membrane based reforming reactor to maintain generally consistent surface temperatures of the oxygen transport membrane tubes and reforming tubes.

When multiple oxygen transport membrane assemblies or modules are arranged within an insulated duct with a heated oxygen-containing gas such as heated air flowing in a cross flow configuration, synthesis gas will be produced provided the requisite steam, fuel, and hydrogen-containing gas are fed to the process side. Sufficient thermal coupling or heat transfer between the heat-releasing ceramic oxygen transport membrane tubes and the heat-absorbing catalyst containing reformer tubes must be enabled within the design of the assemblies or modules and the arrangement of multiple modules in an array. Between about 75% and 85% of the heat transfer between the ceramic oxygen transport membrane tubes and the adjacent catalyst containing reformer tubes is through the radiation mode of heat transfer whereby surface area, surface view factor, surface emissivity, and non-linear temperature difference between the tubes, i.e. $T_{otm}^4 - T_{reformer}^4$, are critical elements to the thermal coupling. Surface emissivity and temperatures are generally dictated by tube material and reaction requirements. The surface area and radiation view factor are generally dictated by tube arrangement or configuration within each module and the entire reactor. While there are numerous tube arrangements or configurations that could meet the thermal coupling requirements between the oxygen transport membrane tubes and the reformer tubes, a key challenge is to achieve a relatively high production rate per unit volume which, in turn, depends on the amount of active oxygen transport membrane area contained within the unit volume. An additional challenge to achieving the optimum thermal coupling performance is to ascertain and optimize the size of the ceramic oxygen transport membrane tubes and the catalyst containing reformer tubes, and more particular the effective surface area ratio, $A_{reformer}/A_{otm}$, of the respective tubes. Of course, such performance optimization must be balanced against the manufacturability requirements, costs, as well as the reliability, maintainability, operating availability of the modules and reactor.

It has been found that significant advantages in these problem areas may be gained by increasing the oxygen transport membrane repeating unit capacity, reduction in catalytic reactor tube diameter, and the module design and tube arrangement. With a reduction in catalytic reactor tube outside diameter from 2.0 to 3.0 inches found in various prior art systems to an outside diameter range of 0.6 to 1.0 inches together with a corresponding change in tube arrangement, the amount of active oxygen transport membrane area contained within a unit volume of reactor housing may be dramatically increased.

Figure 4:
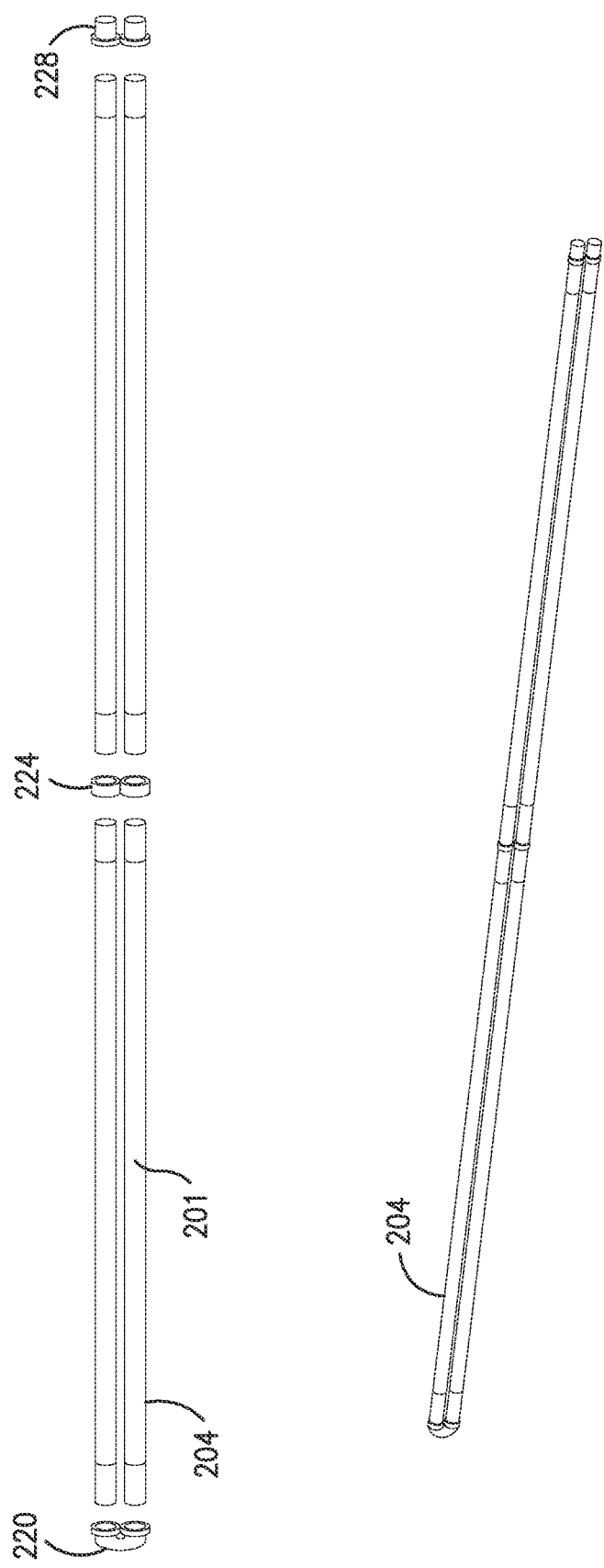
FIG. 4 is schematic illustrations of coupled oxygen transport membrane tubes or oxygen transport membrane repeating units.
Figure 5:
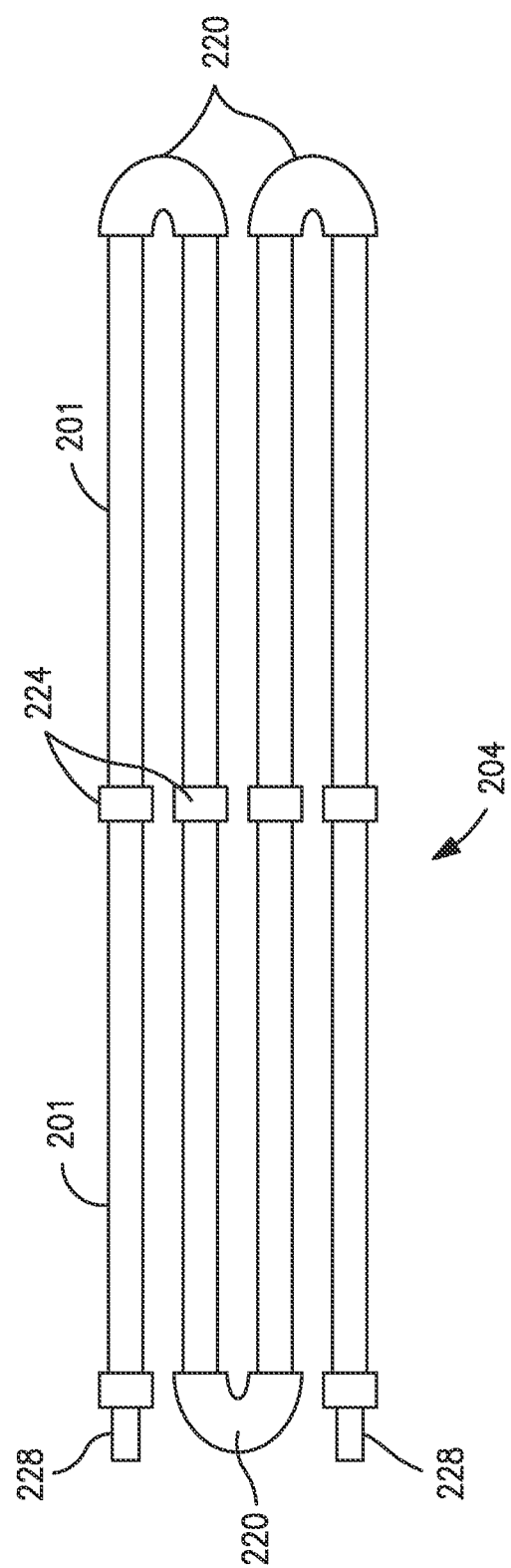
FIG. 5 is schematic illustrations of an alternate embodiment of an oxygen transport membrane repeating units coupling a plurality of oxygen transport membrane tubes.
Figure 6:
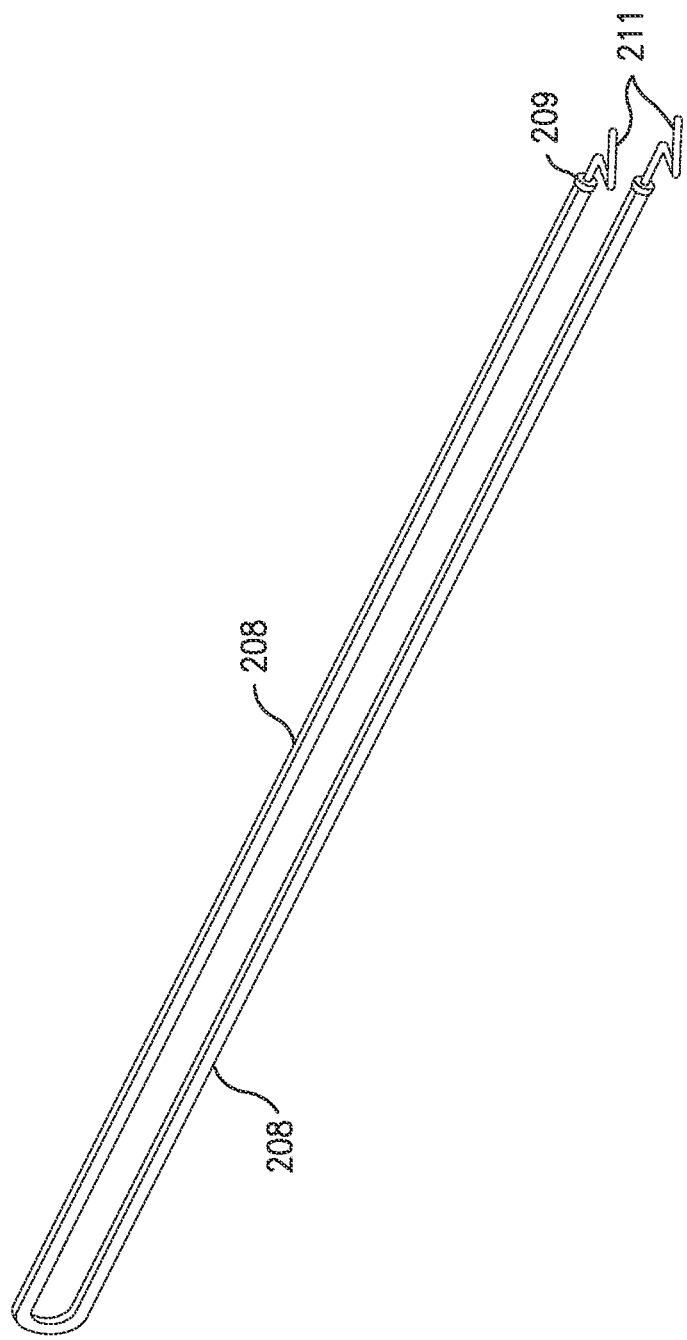
FIG. 6 is schematic illustrations of a catalytic reforming tube or repeating unit.
Figure 7:
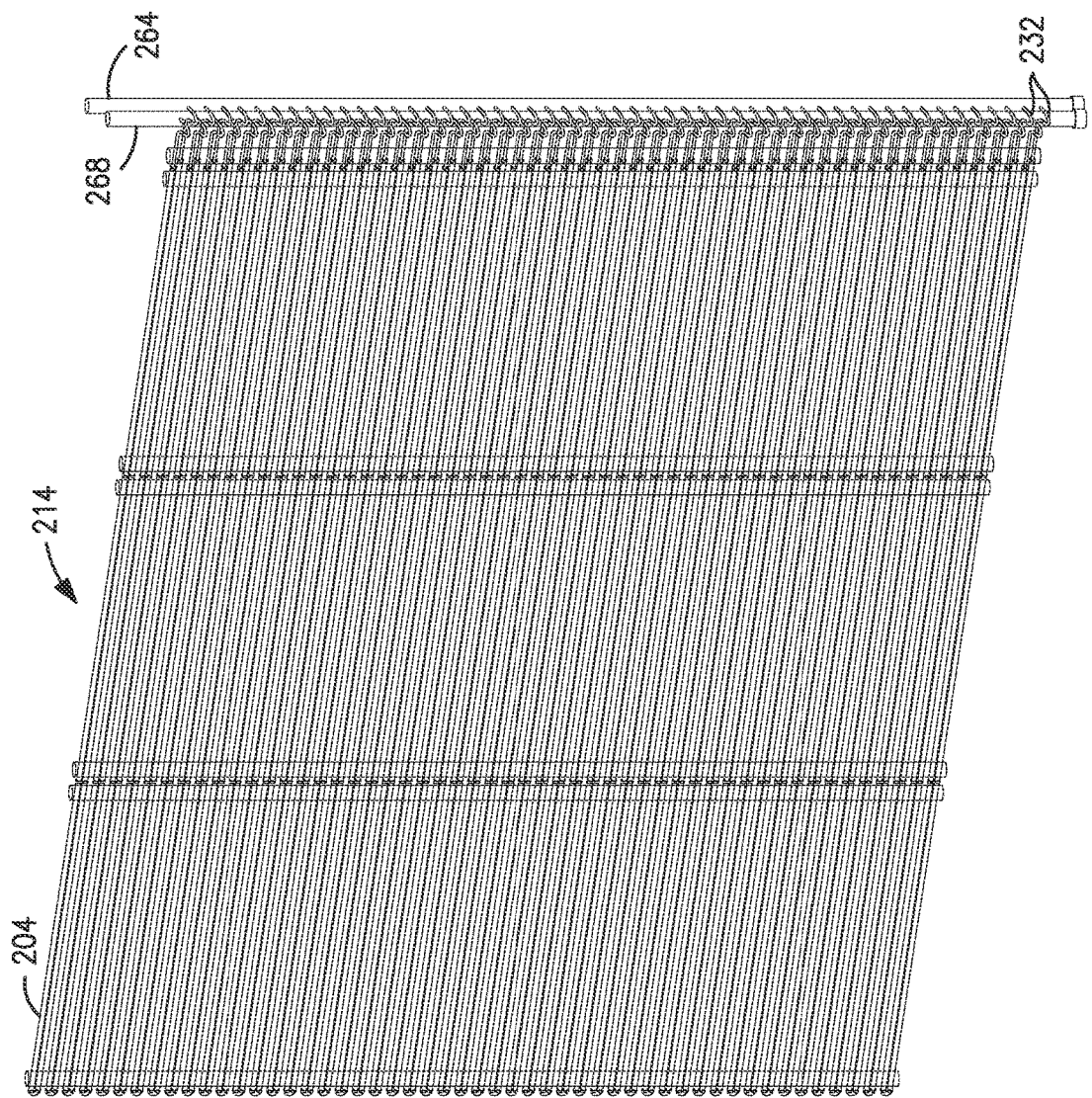
FIG. 7 is a schematic illustration of an oxygen transport membrane panel.
Figure 8:
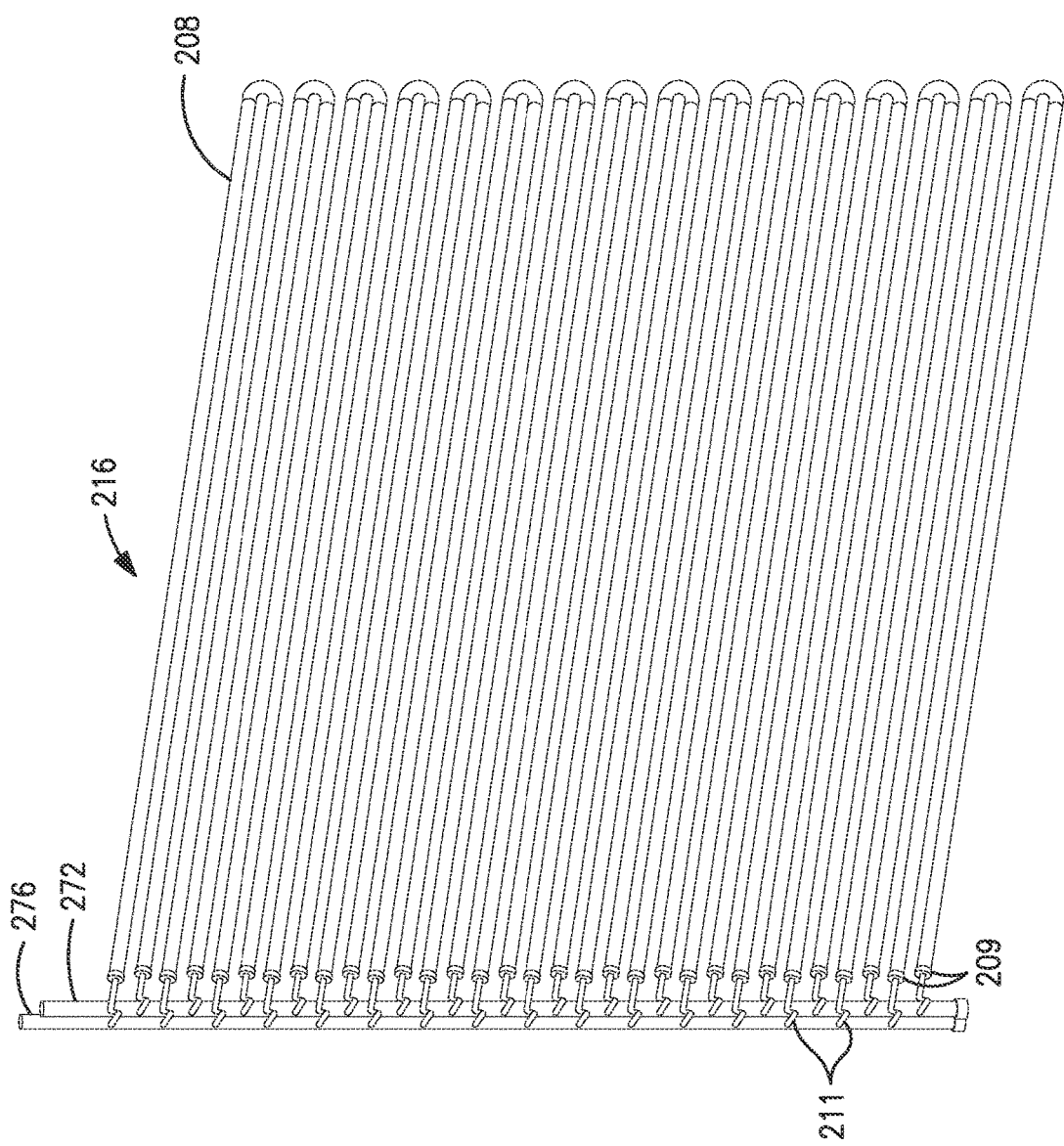
FIG. 8 is a schematic illustration of a catalytic reforming panel.

A preferred arrangement of oxygen transport membrane tubes 201 is a first panel arrangement comprising a plurality of straight rows oxygen transport membrane tubes 204 as generally shown in FIGS. 4, 5 and 7 adjacent to a second panel arrangement comprising plurality of straight rows of catalyst containing reformer tubes 208 as shown in FIGS. 6 and 8. This multiple panel arrangement of oxygen transport membrane tubes and catalyst containing reformer tubes illustrated in FIG. 9 improves the surface area ratio, view factor and radiative heat transfer efficiency between the different tubes. Due to the improved view factor between oxygen transport membrane tubes and reforming tubes, the net tube count and overall tube area of the reforming tubes may be reduced by a factor of 30% to 40% compared to prior art designs. In addition, with a reduction in reforming tube diameter, the required wall thickness to resist creep rupture at the operating temperatures and pressures may be reduced which, coupled with tube count reductions results in significant cost reduction.

As shown in more detail in FIG. 4, a preferred coupling arrangement for any final form of the ceramic tubular membrane elements is referred to as a 'hair-pin' arrangement 204 created by adjoining two tubular membrane elements 201 together in pairs with a 180 degree elbow fitting 220 on one end. This 'hair-pin' arrangement represents a repeating unit of the ceramic oxygen transport membrane element. An alternative preferred arrangement is another multi-pass or serpentine arrangement shown in FIG. 5 and referred to as the 'M-pin' arrangement. The illustrated 'M-pin' arrangement comprises at least four (4) oxygen transport membrane tubes or multi-tube leg segments connected in series, including appropriate ceramic to ceramic adapters 224, and two (2) ceramic to metal adapters 228 configured to sealably connect the ends of the 'M-pin' arrangement to form the oxygen transport membrane panel using advanced metal to ceramic seals. The 'M-pin' arrangement further preferably includes a plurality of ceramic U-shaped connectors configured for fluidically coupling adjacent tubes or leg segments, although a single integrated connector assembly could be used. The leg segments can be of equal lengths or different lengths. The illustrated embodiment shows the use of three (3) ceramic U-bend connectors 220 to couple the adjacent tubes to yield the serpentine arrangement. The multi-pass 'M-pin' arrangement is preferred from a manufacturability and durability standpoint Employing the 'hair-pin', two-pass, M-pin or other multi-pass arrangement also allows for creating higher capacity repeating units by adjoining multiple tubes together using ceramic connectors 224 to create additional effective length of the active ceramic oxygen transport membrane elements as shown in FIG. 7. As discussed in more detail below, the end opposite one of the 'hair-pin' ends of the repeating unit is configured to connect to the feed and exhaust manifolds via small metal tubes 232. By placing all the membrane element external connections at a single end of the module allows thermal expansion of the module without placing additional stress on the connections points. Since the oxygen flux along the reacting length of the tubular membrane element is not constant due to progressive oxidation of the fuel gases occurring along the length of the tubular membrane element, this two-pass arrangement in the repeating unit helps to balance temperatures as the more reactive sections of a repeating unit located proximate the feed is adjacent to the less reactive sections of the same repeating unit located near the exit. At the 'hair-pin' end, the adjacent sections are both moderately reactive. The multi-pass repeating unit is constructed by coupling tube ends through a dense ceramic adapter element 224 or dense ceramic 180-degree elbow fitting 220 with glass-ceramic seals that are crystallized during the membrane element assembly firing process. The 180-degree elbow 220 is a dense ceramic part generally produced through ceramic-injection molding and joining processes.

To assemble an oxygen transport membrane panel assembly, the manifolds are first placed into a frame support on a single side and the plurality of oxygen transport membrane repeating units, already as sealed sub-assemblies, are placed into the engagement or retention features in the frame support with the metal tubing ends inserted into the ports or sockets of the corresponding manifold. The plurality of OTM tubes 204 are then welded to the inlet 268 and outlet manifolds 264 and the outlet manifolds are welded to the frame members at the top and bottom of the panel. To minimize stress due to thermal expansion, the outlet manifold is welded to the frame in only one position.

A similarly constructed second panel may be formed from catalytic reformer repeating units 208 (See FIGS. 6 and 8). In this case, the reforming tube 208 is constructed using metal tubing or pipe preferably made from a suitable wrought material like Incoloy 800HT. These tubes can be oval, substantially cylindrical, or cylindrical in structure. A continuous length of 0.75 inch tubing or 0.5 NPS pipe can be bent to form two parallel legs and a 180-degree turn at one end. This two parallel leg arrangement provides a multi-pass reforming of the feed that intensifies the reforming process while maintaining excellent thermally coupling with the adjacent radiant heat generating oxygen transport membrane tubes. As seen in the drawings, the catalytic reforming tubes are configured as a serpentine tube, or more preferably a U-shaped tube, containing steam methane reforming catalysts and the reactors are arrayed in cross-flow arrangement with the air stream. This two pass flow design provides more residence time, increases surface area and serves to improve the radiative view factor between the oxygen transport membrane and catalytic reforming reactors.

The plurality of reforming tubes 208 are preferably welded to the inlet manifold 272 and outlet manifold 276. The inlet manifold 272 and the outlet manifold 276 are welded to the frame members at the top and bottom of the panel. To minimize stress due to thermal expansion, the outlet manifold is preferably welded to the frame in only one position. In one embodiment, that position is at the top of the panel. End caps 209 facilitating the transition from the reformer tubes to smaller diameter metal tubing pigtails 211 are also welded or brazed onto the reforming tube to complete the catalytic reformer repeating unit.

Figure 9:
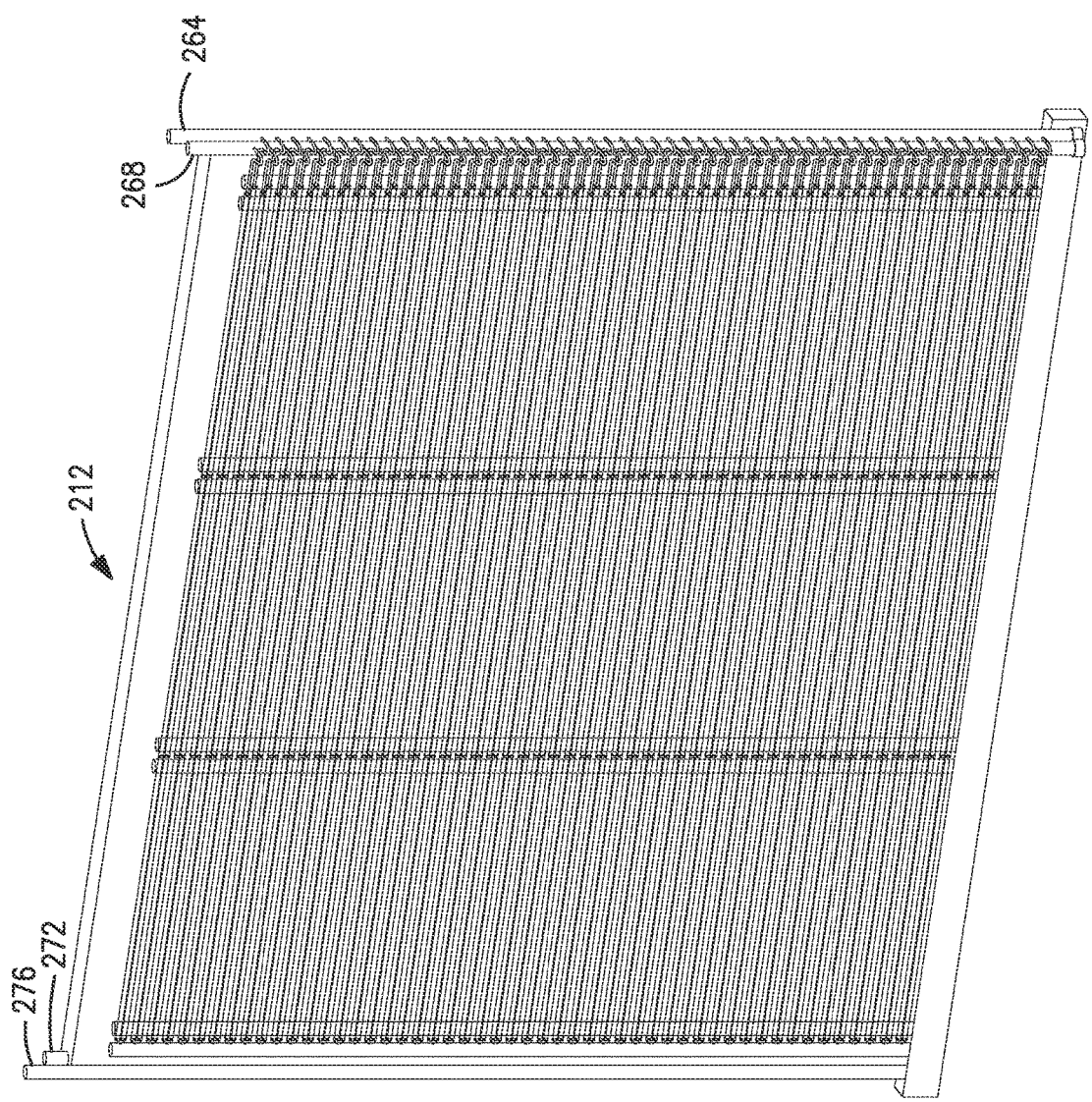
FIG. 9 is a schematic illustration of a dual panel module.
Figure 10:
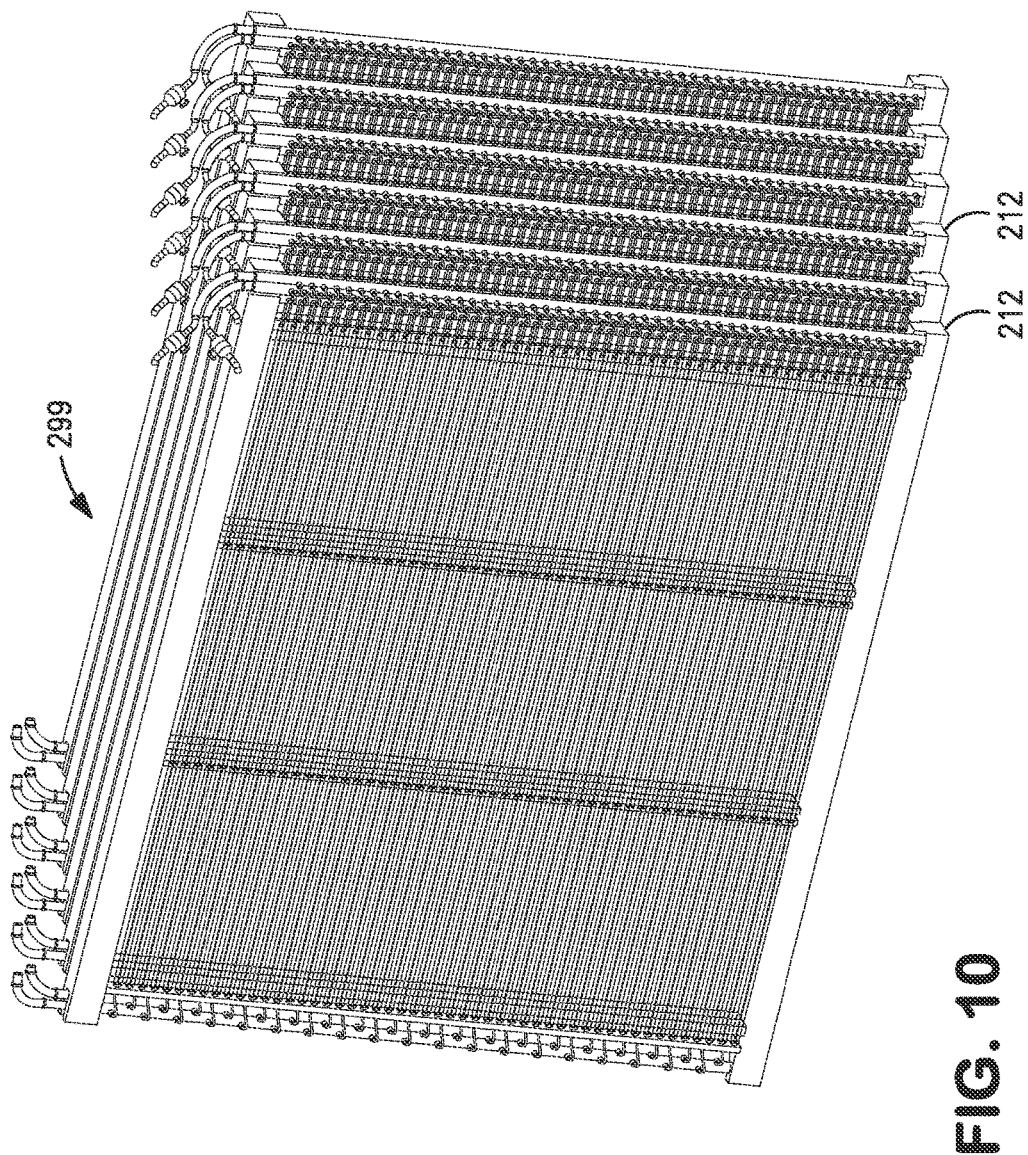
FIG. 10 is a schematic illustration of a plurality of closely packed or stacked dual panel modules.

As seen more clearly in FIGS. 9 and 10, the improved oxygen transport membrane module 212 includes a first oxygen transport membrane panel 214 and a closely arranged second reformer panel 216. This closely coupled arrangement allows for the significant advantages associated with linear row tube or co-planar tube arrangement and with reduced diameter reforming tubes. The illustrated oxygen transport membrane module 212 also has the additional advantages of being inherently modular and expandable in its approach which enables commercial-scale applications without losing efficiency.

The first oxygen transport membrane panel 214 and the second catalytic reformer panel 216 are preferably stacked or nested together to form a dual panel module 212 with the rows of oxygen transport membrane tubes 204 disposed juxtaposed or adjacent to the rows of catalytic reformer tubes 208. One or more of these dual panel modules 212 may be stacked together to form an array of oxygen transport membrane tubes interleaved with an array of catalytic reformer tubes (See FIG. 10). This array 299 has a characteristically high view factor between the oxygen transport membrane tubes and catalytic reformer tubes and a relatively low number of catalytic reformer tubes required to achieve thermal balance. In the preferred array 299, there is preferably between about two and four, and more preferably three or four oxygen transport membrane tubes per catalytic reformer tube. The inlet manifold 264 and exit manifold 268 for the oxygen transport membrane panel 214 and the inlet manifold 272 and exit manifold 276 for the catalytic reformer panel 216 are preferably on opposite sides of the combined panel or dual panel module 212 when fully assembled. This arrangement facilitates simplified manifold connections as well as a reduced thickness and tighter array for the combined panel or dual panel module 212. Although not shown, the oxygen transport membrane panels 214 and catalytic reformer panels 216 may alternatively be arranged in a single panel module with alternating layers in lieu of the dual panel subassembly arrangement.

Figure 11:
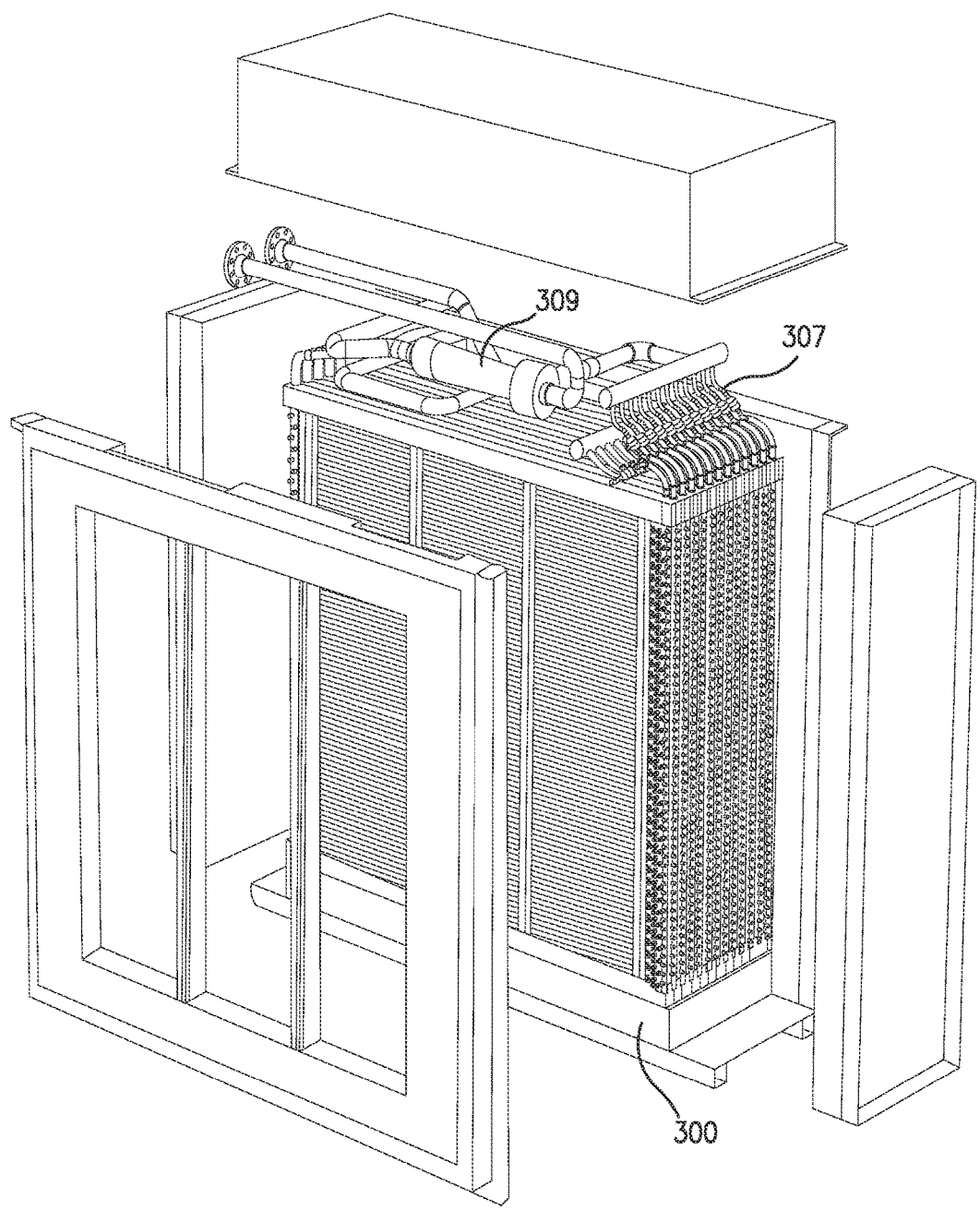
FIG. 11 is a exploded isometric view of an oxygen transport membrane reactor pack assembly.
Figure 12:
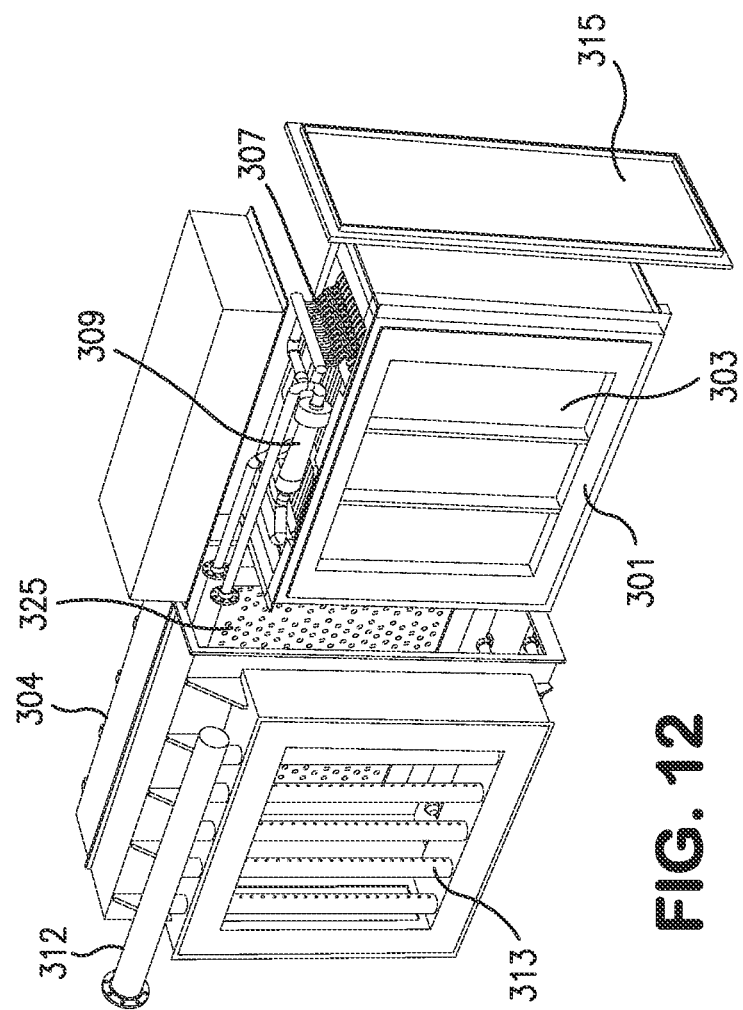
FIG. 12 is a exploded isometric view of an oxygen transport membrane reactor pack assembly and corresponding furnace segment with air staging provision.

The combination of a single oxygen transport membrane panel 214 and a single catalytic reformer panel 216 into a dual panel module 212 forms a basic modular unit of oxygen transport membrane based reforming reactor. Coupling or integrating multiple dual panel modules increases processing capacity and thus synthesis gas production capacity. For any application of the oxygen transport membrane based reforming reactor, the exact panel size and number of dual panel modules may be chosen to best fit the requirements. However, most practical applications of the oxygen transport membrane based reforming reactor may require a large number of panels. To that end, an additional level of integration and modularization is depicted in FIG. 11 and FIG. 12, where multiple dual panel modules 212 are stacked within a refractory-lined steel container or housing 301 and coupled together in to form an easily installed and connected oxygen transport membrane based reforming reactor pack assembly 300. Advantageously, these oxygen transport membrane based reforming reactor pack assemblies 300 can be produced or fabricated in a shop and transported to the plant site for installation. In addition, these multiple module pack assemblies 300 facilitate simplified handling, connecting, and servicing for plant personnel as they are easily installed or removed.

As depicted in FIGS. 11 and 12, one or more of the dual panel modules 212 can be stacked together in a refractory lined housing 301 to form the core of a pack assembly 300. Between six and twenty dual panel modules 212 are preferably stacked within each pack assembly 300. The housing 301 is preferably a carbon steel structure that provides an open window areas 303 to allow air or other oxygen containing stream to flow across the oxygen transport membrane tubes 204 and through the dual panel modules 212. The housing 301 also has refractory lining partially surrounding the stacked dual panel modules and configured to provide thermal insulation between the high temperature region containing the dual panel modules panels and a dedicated section or zone 307 of the pack assembly configured to contain the inlet circuit, outlet circuit and recycle circuit. The pack assembly housing 301 also provides the structural support, access panels, lift points, etc. The multiple dual panel modules 212 within a pack assembly 300 are typically manifolded together within the pack assembly in the dedicated section or zone 307 of the pack assembly, preferably located above or on top of the dual panel modules 212. This dedicated section or zone 307 preferably includes an inlet circuit is configured or adapted to provide a mixed-preheated-feed (e.g. natural gas and steam) to the feed manifolds associated with the catalyst reformer panels and oxygen transport membrane panels and an outlet circuit configured or adapted to receive and withdraw the synthesis gas produced in the catalyst containing reformer panels. The dedicated section or zone also includes a recycle circuit 309 is adapted to provide a portion of the synthesis gas from the exit manifolds of the catalytic reformer panels to the feed manifold associated with the oxygen transport membrane panels.

Oxygen Transport Membrane Furnace Train

As seen more clearly in FIG. 12, each oxygen transport membrane based reforming reactor pack assembly 300 is envisioned to slide into a hot box or furnace segment 304. These furnace segments 304 may be produced individually and connected together in series to form an oxygen transport membrane furnace train 308 (See FIGS. 13-15). Alternatively, a single long hot box or furnace configured to accept multiple oxygen transport membrane based reforming reactor pack assemblies 300 may be fabricated and shipped to the plant or constructed on site. In either embodiment, the oxygen transport membrane based reforming reactor packs 300 are generally installed in series in the oxygen transport membrane furnace train 308. Multiple oxygen transport membrane furnace trains 308 may be arranged in parallel to form a large-scale reformer 309 as shown in FIG. 15. In furnace train 308 arrangements comprising two or more oxygen transport membrane based reforming reactor pack assemblies 300, it may be advantageous to provide an air staging system to provide supplemental cooling air or trim air as well as furnace pressure relief means between adjacent multiple oxygen transport membrane based reforming reactor pack assemblies 300 in the furnace train 308.

For example, an oxygen transport membrane furnace train can be designed to optimize the air temperature control. In the embodiments illustrated in FIGS. 9, 10, and 11, the oxygen transport membrane furnace train includes a heated air intake duct 320, a modular furnace train 308 comprised of a plurality of furnace duct segments 304, a plurality of cooling air supply manifolds 312 operatively coupled to each the plurality of furnace duct segments 304, a plurality of oxygen transport membrane based reforming reactor pack assemblies 300 arranged in series and disposed in the furnace duct segments 304; and an oxygen depleted air outlet or exhaust duct 330.

The furnace duct segment 304 preferably comprises a steel housing with an access panel 315 and an interior chamber configured to receive and contain an oxygen transport membrane based reforming reactor pack assembly 300, generally described above. Each furnace duct segment 304 also provides a front and rear window to allow the oxygen containing air streams to flow through the oxygen transport membrane pack assembly 300 and in a cross flow arrangement with the oxygen transport membrane tubes and reforming tubes. Each furnace duct segment 304 also includes a cooling air inlet circuit operatively connected to a cooling air control valve (not shown), cooling air distribution manifolds 312, cooling air distribution tubes 313 and air diffuser screens 325.

The supplemental cooling air is preferably introduced through a tube or pipe based cooling air system such that the cooling air is distributed within a cross-section of each furnace duct segment 304 through a plurality of distribution tubes 313 or perforated cylinders disposed proximate the front window of each furnace segment 304. The placement of the distribution tubes 313 relative to the oxygen transport membrane based reactor is such that there is sufficient length downstream of the cooling air injection point to allow for adequate mixing of the supplemental cooling air with the incoming heated air stream prior to contacting the oxygen transport membrane tubes. Such mixing is further enhanced through vortex shedding behind the larger diameter distribution tubes 313 or perforated cylinders. Such mixing of the supplemental cooling air with the heated air stream allows for effective control of the temperature within each furnace segment 304.

Each furnace duct segment also includes one or more air diffuser screens 325 disposed proximate the back window or distal end of the furnace segment 304. This air diffuser screen 325 is a perforated board or screen preferably constructed of refractory board material. Refractory materials such as Duraboard™ HD from Unifrax Inc. or calcium-silicate material from Zircar Inc. are examples of refractory material. The air diffuser screen 325 is configured to allow the oxygen depleted residual stream exiting the oxygen transport membrane based reactor to exit the furnace duct segment while retaining much of the heat within the furnace duct segment 304.

The supplemental cooling air may be supplied by a blower to a main cooling air header (not shown) and cooling air flow to the cooling air manifold 312 and cooling air distribution tubes 313 is preferably controlled through a simple low-temperature control valve, such as a butterfly valve (not shown). Alternatively, where the oxygen transport membrane furnace train is operating at less than ambient pressure, the cooling air may be supplied from a source of filtered ambient air, controlled through the same control valves, but without the main cooling air header and blower.

Temperature control in the oxygen transport membrane based reactor is achieved through a combination of two distinct system features. First, by introducing a flow of supplemental cooling air to the heated oxygen containing stream at locations upstream of the plurality oxygen transport membrane based reactors in a multi-stage reactor system and mixing the flow of supplemental cooling air with the heated oxygen containing streams introduced to each of the plurality oxygen transport membrane based reactors in a multi-stage reactor system, it is possible to maintain the oxygen containing feed to each oxygen transport membrane based reactor at a uniform temperature. The resulting mixed stream is passed across the surfaces of a plurality of oxygen transport membrane elements within each reactively driven oxygen transport membrane based reactor wherein the some oxygen is depleted from the mixed stream to produce a residual stream at a temperature generally above the temperature of the mixed stream.

The residual stream is then passed through a refractory air diffusion screen disposed downstream of and proximate the distal end of the reactively driven oxygen transport membrane based reactor. The refractory air diffusion screen is configured to retain the heat generated by the reactively driven oxygen transport membrane based reactor while concurrently allowing the residual stream to pass therethrough Advantages of the disclosed air temperature control scheme and supplemental cooling air arrangement include an improved surface temperature control for all oxygen transport membrane reforming reactor modules and all reactor/reforming tubes in the furnace train by virtue of the staged cold-air injection between modules without the need to for increased heated air to the reactors. In addition, the increase in total airflow from the mixture of heated incoming air feed with the cooling air reduces the oxygen recovery within a pack which allows for a more constant oxygen partial pressure on the retentate side of the oxygen transport membrane within a pack assembly. Total effective recovery of 50-70% is achieved by putting multiple packs in series.

Air temperature control within the entire furnace train is an important aspect to controlling the overall performance of the oxygen transport membrane based reforming reactors disposed therein. In fact, air temperature control affects both the performance of the oxygen transport membrane tubes as well as the reforming tubes. It has been found that for each 50° C. rise in incoming air temperature for a given pack translates to about a 100° C. rise in the surface temperatures of the oxygen transport membrane tubes and reforming tubes in the reactors in that pack. Excessive surface temperatures of the oxygen transport membrane elements will lead to earlier membrane failures, shorter operational life and potentially degraded system performance. Similarly, excessive surface temperatures of the reforming tubes may adversely affect the performance of the reforming catalyst and resulting quality of the synthesis gas.

To develop the optimum air temperature control scheme understand the thermal coupling occurring within the above described oxygen transport membrane based reforming reactor. It is known that the heat generated at the surface of the oxygen transport membrane must leave the surface by convective heat transfer to the surrounding and conveyed gases and the radiative heat transfer to the reformer surfaces. This known principle can generally be expressed as:

$$Q_{otm} = Q_{rad} + Q_{conv, air} + Q_{conv, fuel} + Q_{cond};$$

and $$F_r + F_{conv, air} + F_{conv, fuel} = 1$$

where $Q_{otm}$ is heat released at the oxygen transport membrane surface; $Q_{rad}$ is net heat transferred through radiation; $Q_{conv}$, air is heat convected to surrounding air; $Q_{conv}$, fuel is heat convected to fuel gases conveyed within the tube; $Q_{cond}$, is heat lost through conduction which is assumed to be negligible; $F_r$ is the fraction of heat leaving the oxygen transport membrane surface due to radiation; and $F_{conv,air}$ and $F_{conv,fuel}$ are convective losses to air and fuel gases, respectively.

If the heat generated at the surface of the oxygen transport membrane ($Q_{otm}$) is characterized as:

$$Q_{otm} = A_1 N'_{O_2} \times LHV_{fuel}$$

then the net heat lost by the oxygen transport membrane due to radiation and due to convection to the surrounding air could be expressed, respectively as:

$$Q_{rad}/A_1 = N'_{O2} \times LHV_{fuel} \times F_r;$$

and $$Q_{conv,air}/A_1 = N'_{O2} \times LHV_{fuel} \times F_{conv,air}$$

where $A_1$ is the oxygen transport membrane surface area; $N'_{O2}$=oxygen flux across the membrane (sccm/cm2); $LHV_{fuel}$ is the lower heating value of fuel gas supplied to oxygen transport membrane; $F_r$ is the fraction of heat leaving the oxygen transport membrane surface due to radiation; and $F_{conv,air}$ is the fraction of heat leaving the oxygen transport membrane surface due to convection to the surrounding air.

In other words, for any collection of oxygen transport membrane tubes arranged in a furnace or reactor duct, there will be a characteristic air temperature rise across the oxygen transport membrane tubes due to convective coupling to the air stream which cannot be avoided. To operate the oxygen transport membrane based reforming reactor at high oxygen recovery for a fixed oxygen flux, the air flow rates are typically reduced and for a fixed heat input to the air, the air temperature rise is necessarily increased. To mitigate this issue, the total oxygen transport membrane tube area can be broken up into a plurality of packs arranged in series and a specific quantity of cooling air or trim air may be introduced and mixed in between the series of packs to reduce the temperature of the air conveyed to downstream packs.

Also, for a given value of oxygen transport membrane tube surface area and oxygen flux, there is generally a fixed amount of oxygen removed from the airstream by the oxygen transport membrane tubes. This amount of depleted or removed oxygen is characterized by:

$$N_{O2} = (1 \text{ mol } O_2/4.78 \text{ mol air}) \times N_{air} \times U_{air}$$

where $N_{O2}$ and $N_{air}$ are the molar flow rates of oxygen and air respectively, and $U_{air}$ is the fraction of oxygen recovered from the air, or "oxygen recovery".

For a given oxygen flux of $N'_{O2}$, the required airflow per unit of oxygen transport membrane tube surface area is characterized by the equation $N_{air}/A_1 = 4.78 \ N'_{O2}/U_{air}$ and the air temperature rise across the OTM tubes can be determined from the air side heat balance, namely $Q_{conv,air} = N_{air} C_{p,\ air} (\Delta T_{air})$. Expressed on a unit OTM tube surface area basis, air temperature rise across the OTM tubes is characterized as:

$$\Delta T_{air} = (Q_{conv,air}/A_1)/(N_{air}/A_1) C_{p,air};$$

or $$\Delta T_{air} = (U_{air} \times LHV_{fuel} \times F_{conv,air})/(4.78 \times C_{p,air})$$

In short, the air temperature rise across the oxygen transport membrane tubes is generally independent of oxygen flux and oxygen transport membrane surface area and is dependent only on oxygen recovery, air specific heat, heat release at the membrane per unit of oxygen, and the fraction of the heat that is transferred to the air by convection.

For an oxygen transport membrane furnace train of several oxygen transport membrane pack assemblies arranged in series on the airflow side, a specific amount of cooling airflow may be added between adjacent packs to reduce the air temperature for the next pack in the series. If the air temperature rise from the previous pack is to be fully reversed, an estimate of the cooling airflow required is given by:

$$N_{cooling}/N_{air} = C_{p,air}(\Delta T_{air})/C_{p,cooling}(T_{inlet} - T_0)$$

where $N_{cooling}/N_{air}$ is the fraction of cooling air that needs to be added to the air leaving the upstream pack ($N_{air}$), and ($T_{inlet} - T_0$) is the change of temperature from the cooling air source $T_0$, to the inlet air of the downstream pack, $T_{inlet}$.

Figure 16:
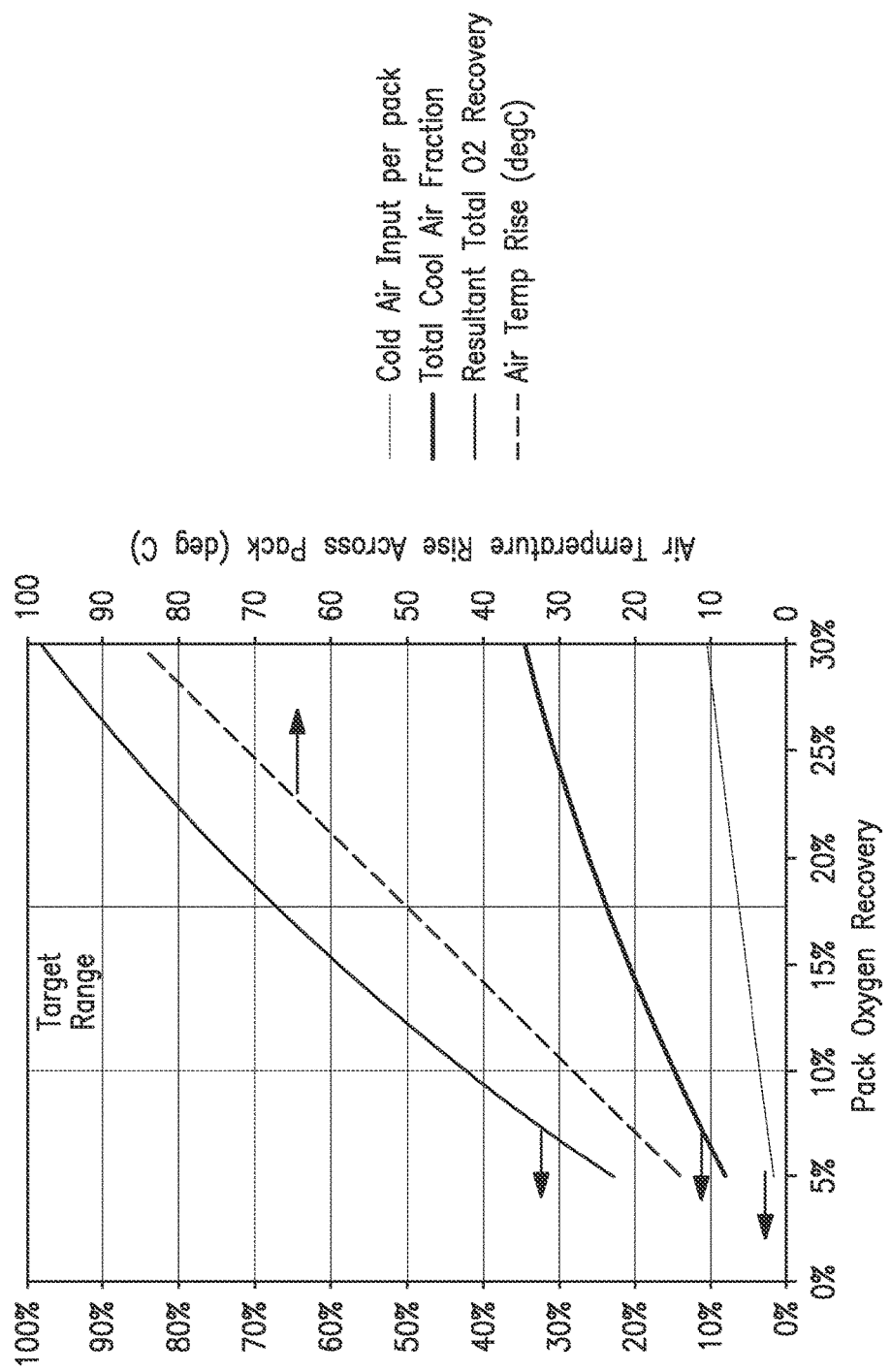
FIG. 16 is a chart that shows selected air temperature control variables as a function of the oxygen recovery in a single pack assembly, including: (i) the cooling air input per pack as a percentage of total air flow; (ii) the total cool air fraction as a percentage of total air flow; (iii) the resultant total oxygen recovery across the entire five-pack furnace train; and (iv) the air temperature rise per pack for a five pack oxygen transport membrane furnace train.

Using the above characterizations, one can predict or model the air temperature rise for the oxygen transport membrane based reforming reactor pack assemblies 300 described above with reference to FIGS. 10-14 and using the predicted fraction of heat transferred by convection to the air stream of 9%. FIG. 16 shows the predicted or modeled results for a five pack oxygen transport membrane furnace train. Specifically, FIG. 16 shows selected air temperature control variables as a function of the oxygen recovery in a single pack assembly, including: (i) the cooling air input per pack as a percentage of total air flow; (ii) the total cool air fraction as a percentage of total air flow; (iii) the resultant total oxygen recovery across the entire five-pack furnace train; and (iv) the air temperature rise per pack for a five pack oxygen transport membrane furnace train.

In FIG. 16, the cooling air input per pack as a percentage of total air flow represents the volume of cooling airflow required to be introduced between reactor pack assemblies to reverse the air temperature rise and maintain the surface temperatures of the oxygen transport membrane tubes and reformer tubes generally consistent across all five reactor packs in the furnace train. The curves illustrated in FIG. 16 suggest that for any collection of oxygen transport membrane tubes running at an oxygen recovery level that is higher than about 17.5%, the air temperature rise across the pack will exceed 50° C. To keep the oxygen transport membrane tubes within a narrow operating temperature range of about 1000° C.-1025° C., it is necessary to limit the air temperature rise across the pack, preferably to an air temperature rise of less than about 50° C.

Put another way, designing and operating the oxygen transport membrane based reforming reactor at about 17.5% oxygen recovery per pack, the air temperature rise at each pack is limited to less than about 50° C. and, more importantly, the overall oxygen recovery is about 67%. The addition of the supplemental cooling air to the oxygen transport membrane furnace train between the packs increases the total amount of air required by the furnace train by approximately 25%. The additional costs associated with the 25% additional air flow is negligible compared to the improvements in the oxygen transport membrane based reforming reactor and system reliability, durability, and improved performance.

Examples

Figure 13:
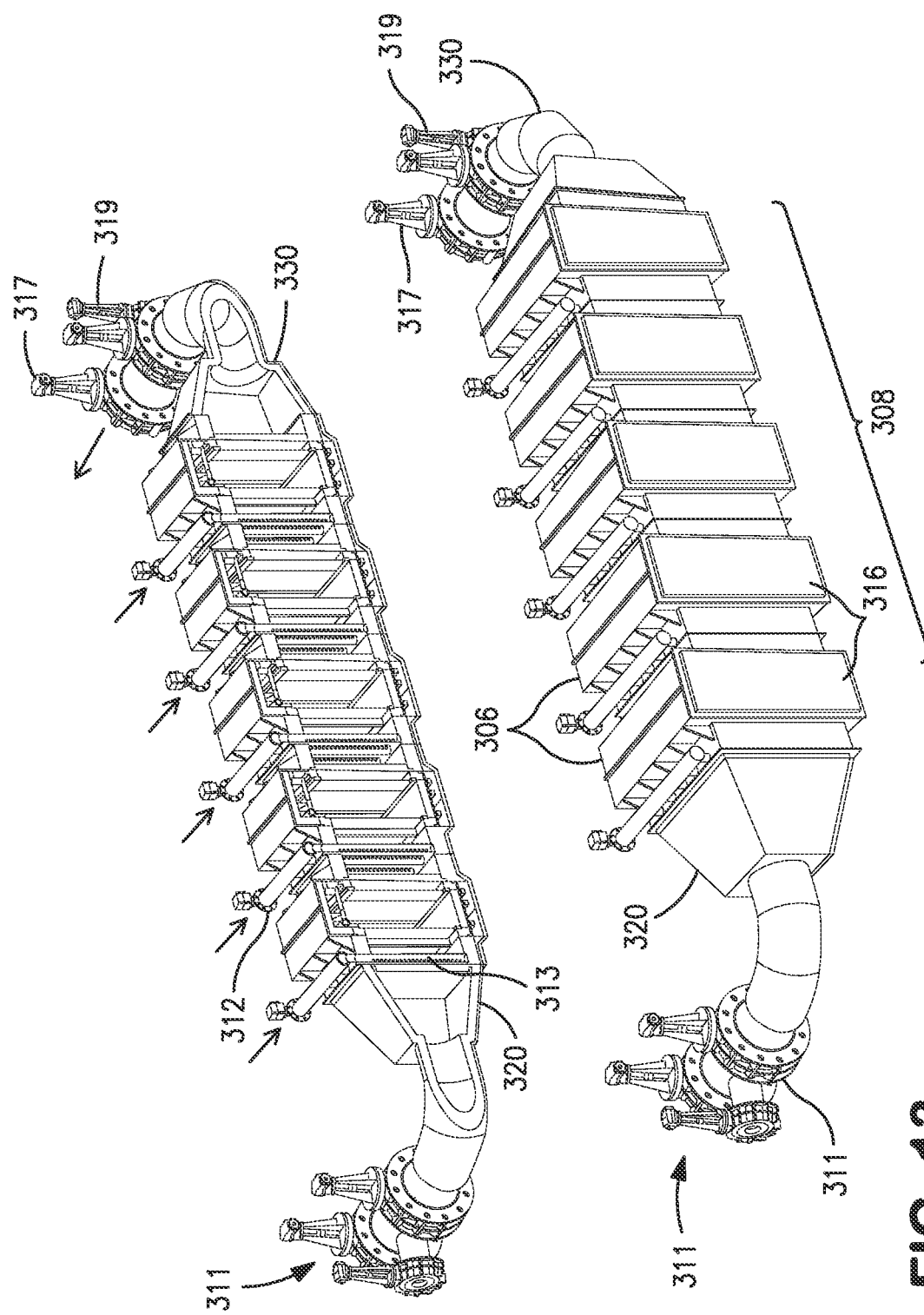
FIGS. 13 and 14 are schematic illustration of a furnace train.
Figure 14:
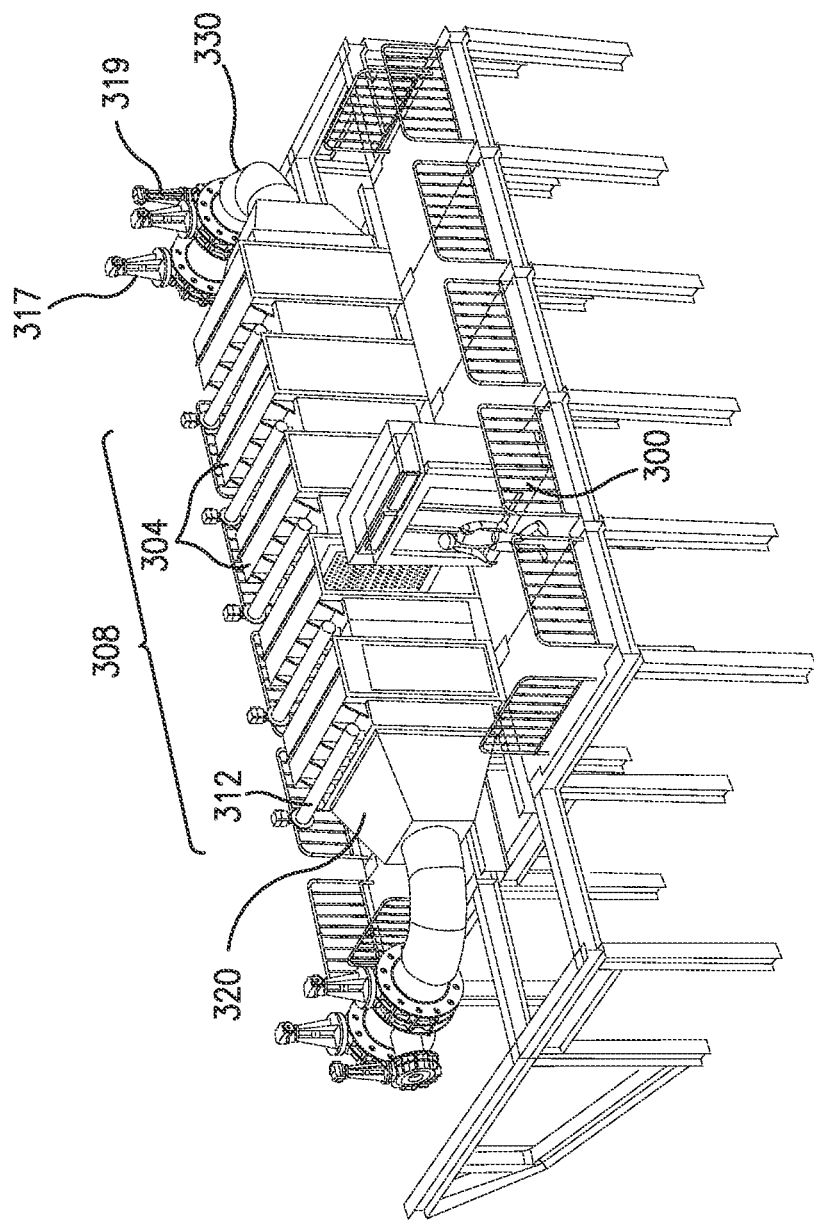
Figure 15:
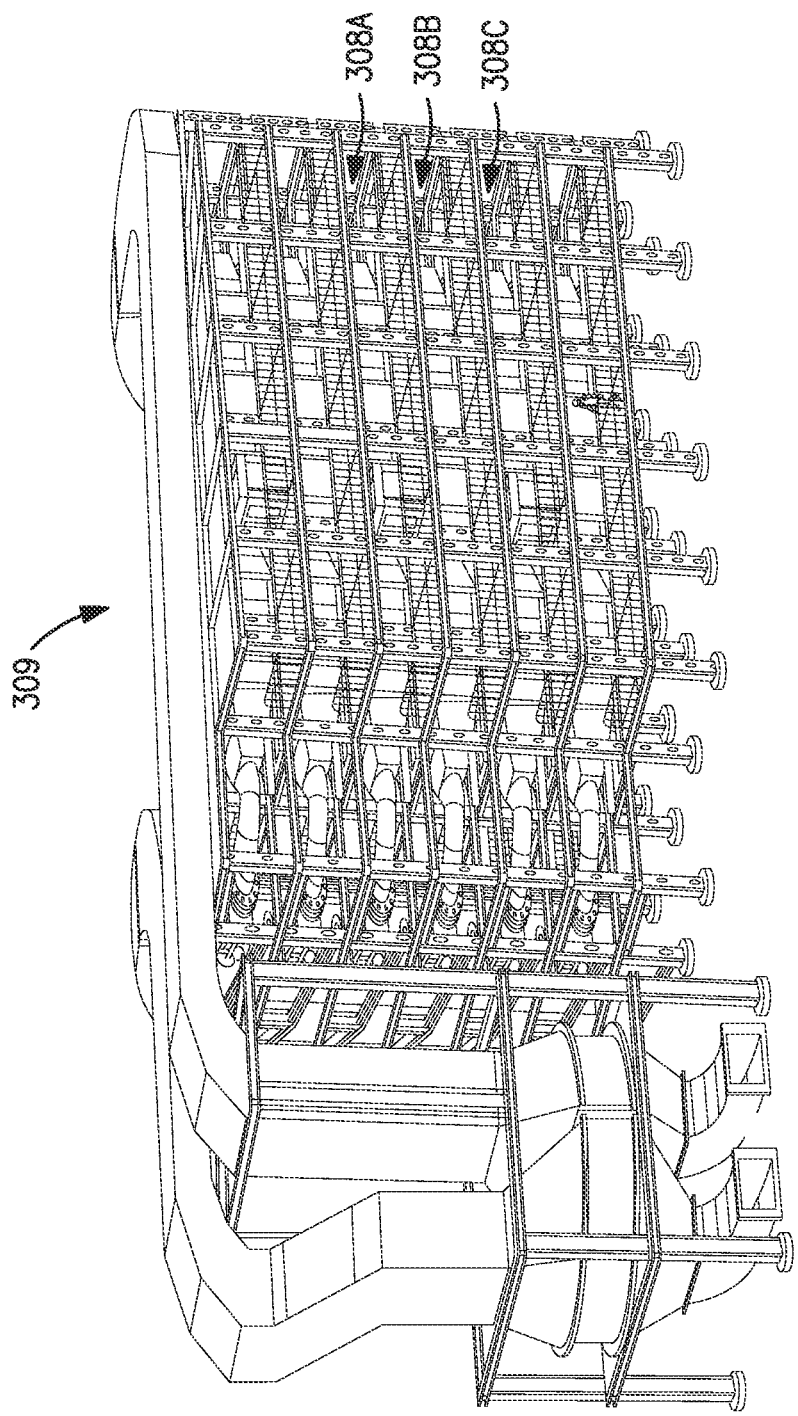
FIG. 15 is a schematic illustration of multiple furnace arrangements in a large-scale synthesis gas production system.

A serial flow air flow through a furnace train, such as those furnace trains illustrated in FIGS. 13-15 would typically involve directing a significant volume of feed air (e.g. 5 MMscfd to 40 MMscfd) heated to a temperature between about 800° C. to 1000° C. through the furnace train. As the air flows through each oxygen transport membrane based reforming reactor pack assembly some of the oxygen is depleted from the stream by virtue of the oxygen transport membrane elements, as generally described above. In addition, some of the heat released in the exothermic oxygen transport membrane reaction is transferred to the passing air stream causing an increase in temperature of the air stream that moves on to the next oxygen transport membrane based reforming reactor pack assembly.

As indicated above, air temperature control is critical to oxygen transport membrane reactor control. It has been found that for each 50° C. rise in incoming air temperature translates to about a 100° C. rise in the surface temperature of the oxygen transport membrane elements for that pack assembly. The air temperature must be preferably controlled to approximately a 50° C. range to keep oxygen transport membrane surface temperatures within the desired operational temperature range. Excessive surface temperatures of the oxygen transport membrane elements will lead to earlier membrane failures, shorter operational life and potentially degraded system performance. Air temperature control is also critical to the catalytic reformer reactor control. Again, for each 50° C. rise in air temperature a 100° C. rise in the wall surface temperature of the reformer tubes within any pack assembly will likely be realized. Precise control of the wall surface temperatures of the reforming tubes is required to keep the reformer temperatures and quality of the synthesis gas at the targeted or designed levels.

Figure 17:
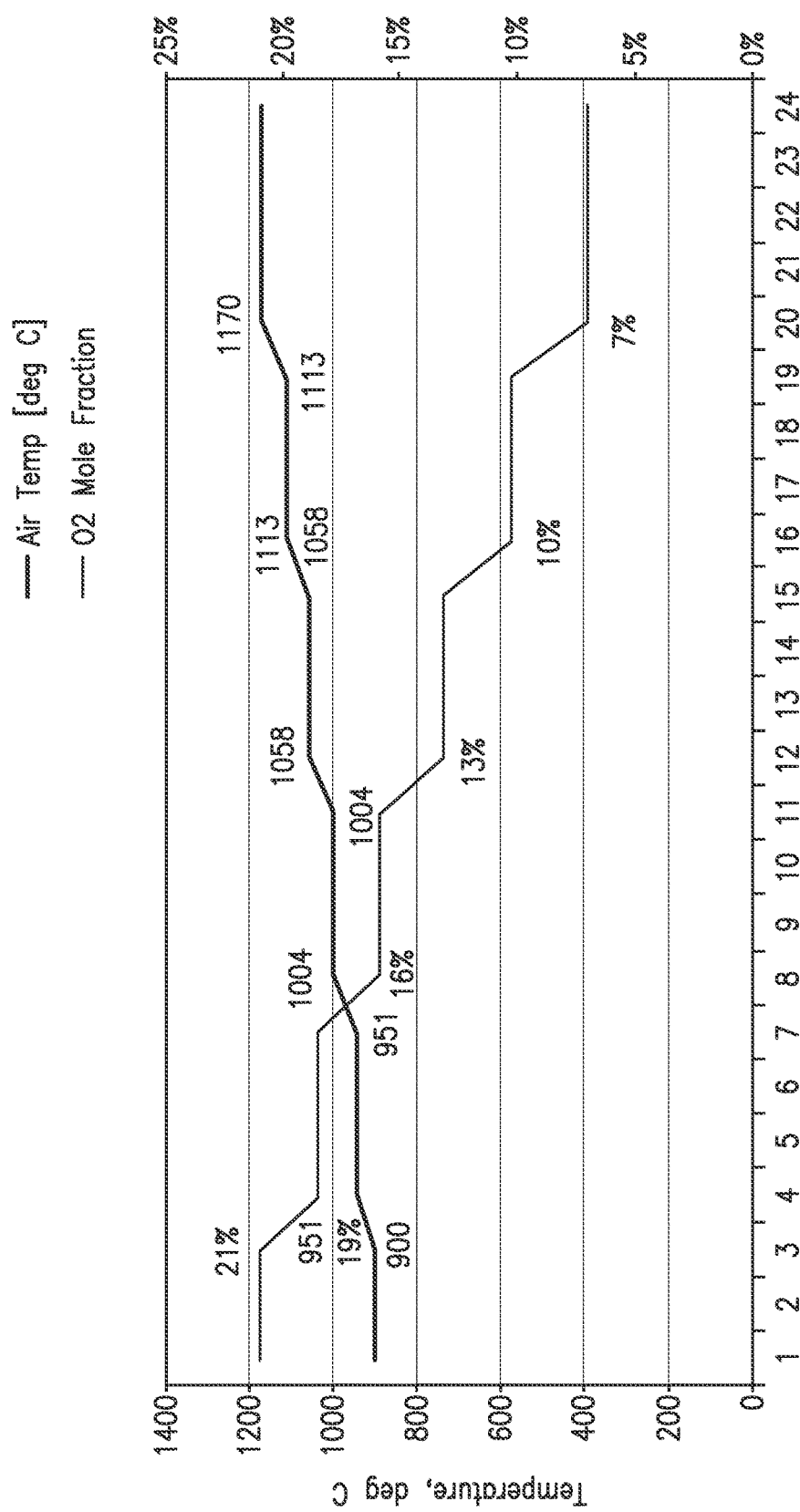
FIG. 17 is a chart that shows the air stream temperature rise at the entrance and exit of five oxygen transport membrane based reforming reactor pack assemblies placed in series in an oxygen transport membrane furnace train as well as the oxygen concentration in the air stream at the entrance and exit of each pack assembly for a baseline case without an air temperature management solution.

FIG. 17 shows the air stream temperature rise at the entrance and exit of each of the five oxygen transport membrane based reforming reactor pack assemblies as well as the oxygen concentration in the air stream at the entrance and exit of each pack assembly. This baseline data was obtained by modeling a serial flow of about 6.4 MMscfd of feed air heated at an incoming temperature of about 900° C. through a five pack furnace train. While this modeled arrangement provides excellent overall oxygen recovery of about 0.899 MMscfd of oxygen or roughly 67% of the available oxygen in the air stream, the overall air temperature increase is too high. The maximum air temperature within the five pack furnace train would reach about 1170° C. representing a temperature rise from inlet to outlet of about 270° C.

Figure 18:
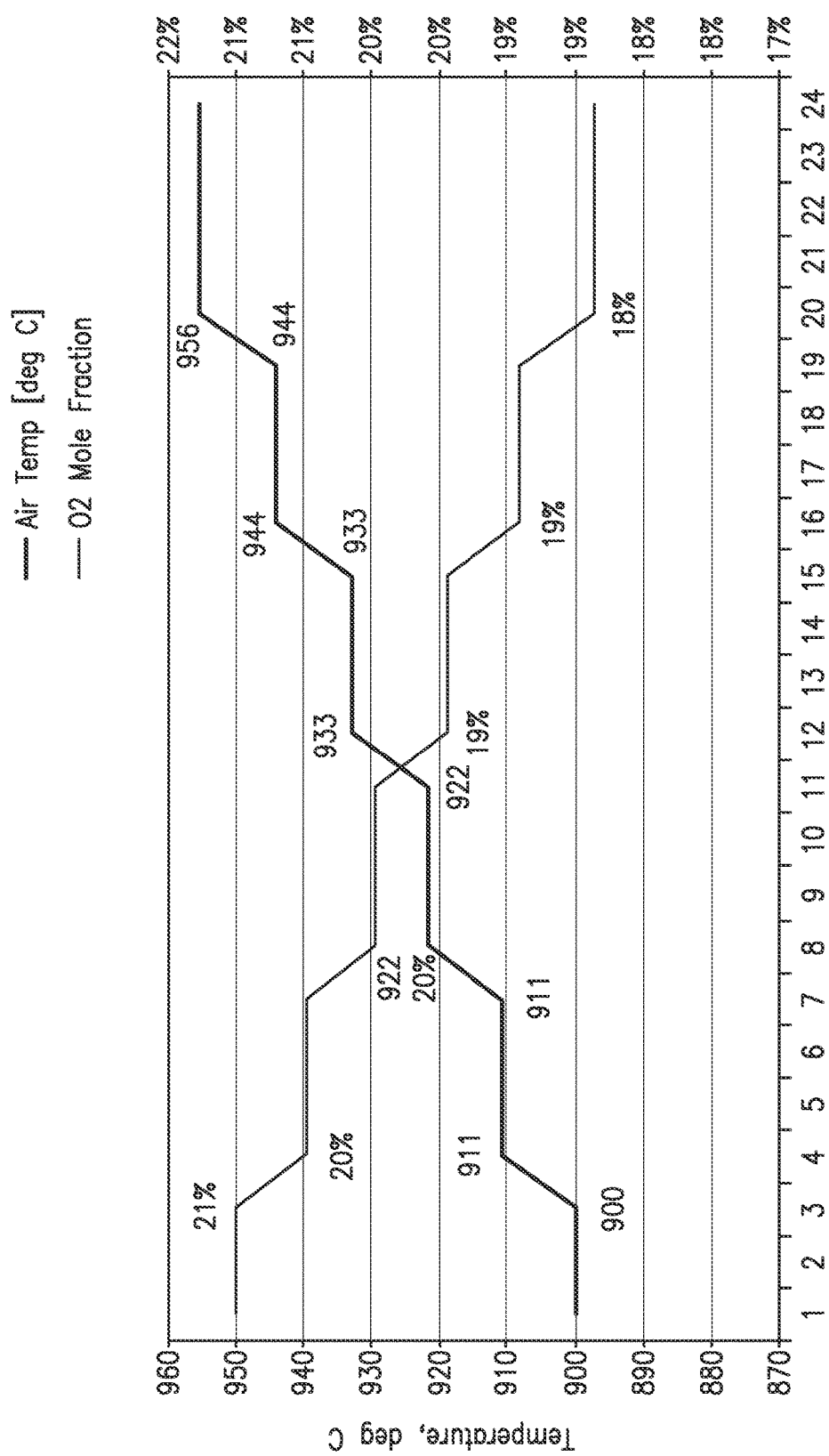
FIG. 18 is a chart that shows the air stream temperature rise at the entrance and exit of each of the five oxygen transport membrane based reforming reactor pack assemblies placed in series in an oxygen transport membrane furnace train as well as the oxygen concentration in the air stream at the entrance and exit of each pack assembly for a conventional solution to air temperature management.

The conventional solution to this excessive temperature rise in an oxygen transport membrane reactor would be to increase the incoming airflow. FIG. 18 shows the air stream temperature rise at the entrance and exit of each oxygen transport membrane based reformer reactor pack assembly as well as the oxygen concentration in the air stream at the entrance and exit of each oxygen transport membrane based reformer reactor pack assembly in an arrangement where the incoming air flow is increased to 30.6 MMscfd of feed air heated to a temperature of about 900° C. While this increase in incoming heated air flow maintains the maximum air temperature slightly higher than desired at about 956° C. or 56° C. above the starting air feed temperature, the increase in the flow of air feed is over 400% or 4 times above the baseline case. This significant increase in air feed flow results in an increase in capital costs associated with compressing and/or handling this air flow as well as an increase in operating costs associated with heating the entire incoming air flow to the target incoming temperature of about 900° C. Disadvantageously, the oxygen recovery realized using this solution is too low at only 14% of the available oxygen.

Figure 19:
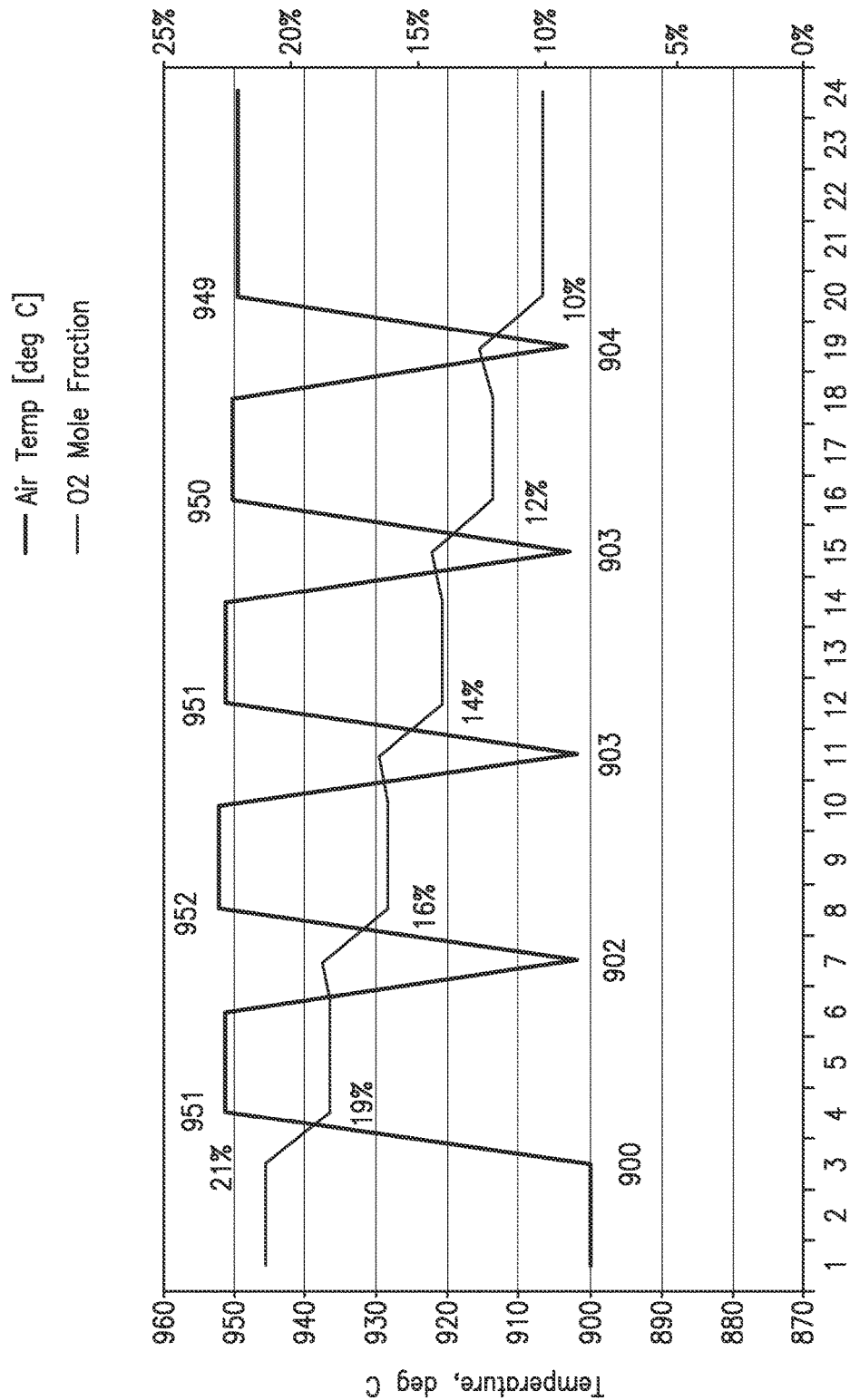
FIG. 19 is a chart that shows the air stream temperature rise at the entrance and exit of each of the five oxygen transport membrane based reforming reactor pack assemblies placed in series in an oxygen transport membrane furnace train as well as the oxygen concentration in the air stream at the entrance and exit of each pack assembly for the solution to air temperature management in accordance with the present invention.

The presently disclosed embodiments use a staged air flow arrangement across the five pack oxygen transport membrane based reforming furnace train. FIG. 19 shows the air stream temperature rise at the entrance and exit of each oxygen transport membrane based reforming reactor pack assembly as well as the oxygen concentration in the air stream at the entrance and exit of each oxygen transport membrane based reforming reactor pack assembly in the staged air flow arrangement. In this arrangement, the flow of the heated incoming air flow serially passing through all five of the pack assemblies is about 6.6 MMscfd at an incoming temperature of about 900° C. In addition roughly 1.6 MMscfd of cold trim air is supplemented into the feed air stream in between adjacent pack assemblies.

By injecting the supplemental cooling or trim air into the heated feed air stream, the maximum air temperature in the multi-pack furnace train is maintained at about 949° C. or within the targeted 50° C. range above the starting air feed temperature. The increase in the total flow of air feed is only 28% above the baseline case and there is no requirement to heat the supplemental air to the high incoming temperature. As a result, the additional capital and operating costs to handle the supplemental air feed is minimal. Advantageously, the oxygen recovery realized using this staged air flow arrangement is 52% of the available oxygen slightly below the baseline case.

Reactively Driven Oxygen Transport Membrane Furnace Train Based

As seen in FIGS. 12-14, the main preheated airflow is introduced to the oxygen transport membrane furnace train 308 through refractory lined ductwork 320 through a double-block and bleed valve arrangement 311 so that heated airflow can be stopped when the furnace train 308 is to be isolated from other parallel operating furnace trains (see 308A, 308B, 308C) and cooled down for service. The double-block-and-bleed air valve arrangement 311 allows for each furnace train 308 to be safely isolated from parallel furnace trains for effective turn-down of synthesis gas production in plants where multiple furnace trains (see e.g. 308A, 308B, 308C) are employed. Similarly, isolation and cool-down of furnace trains 308 that require maintenance or servicing from parallel furnace trains which would continue to produce synthesis gas provides improved plant operating availability. During such turn-down or cool-down operating modes, the inlet air shutoff valve is closed and the supplemental cooling air manifolds 312 are fully opened to flush the isolated furnace train and associated reactor modules or packs disposed therein with cooled air. The exit shut off valve 317 is also closed to prevent the cooled flush air from recirculating back to the ceramic regenerator while the other exit valves 319 including the bleed valve is open so the flush air is purged from the system.

Reactively Driven Oxygen Transport Membrane Based Boiler or Process Gas Heater

In another aspect, the present invention may be characterized as a system and method for air temperature control in an oxygen transport membrane based steam generating reactor or process gas heating reactor for producing steam or other heated process fluid. The improved reactor and system provides air cooling and temperature management of the reactor in a manner similar to the above-described oxygen transport membrane based reforming reactors.

Figure 3C:
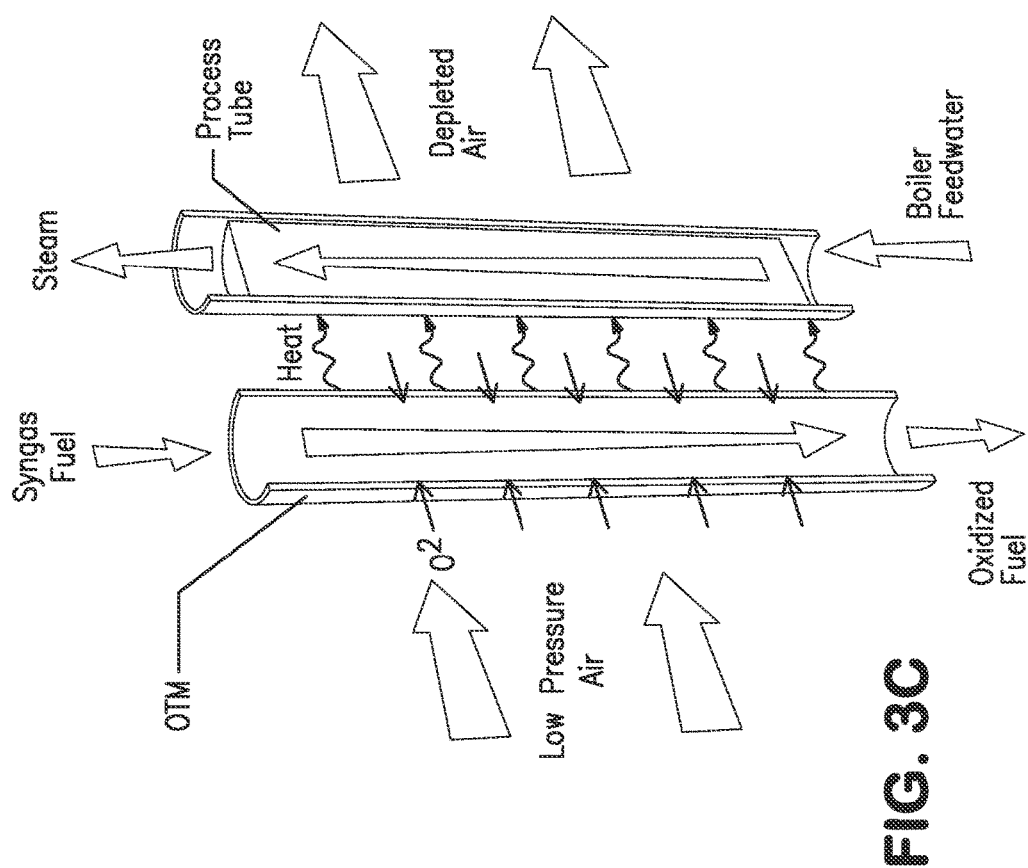
Figure 3D:
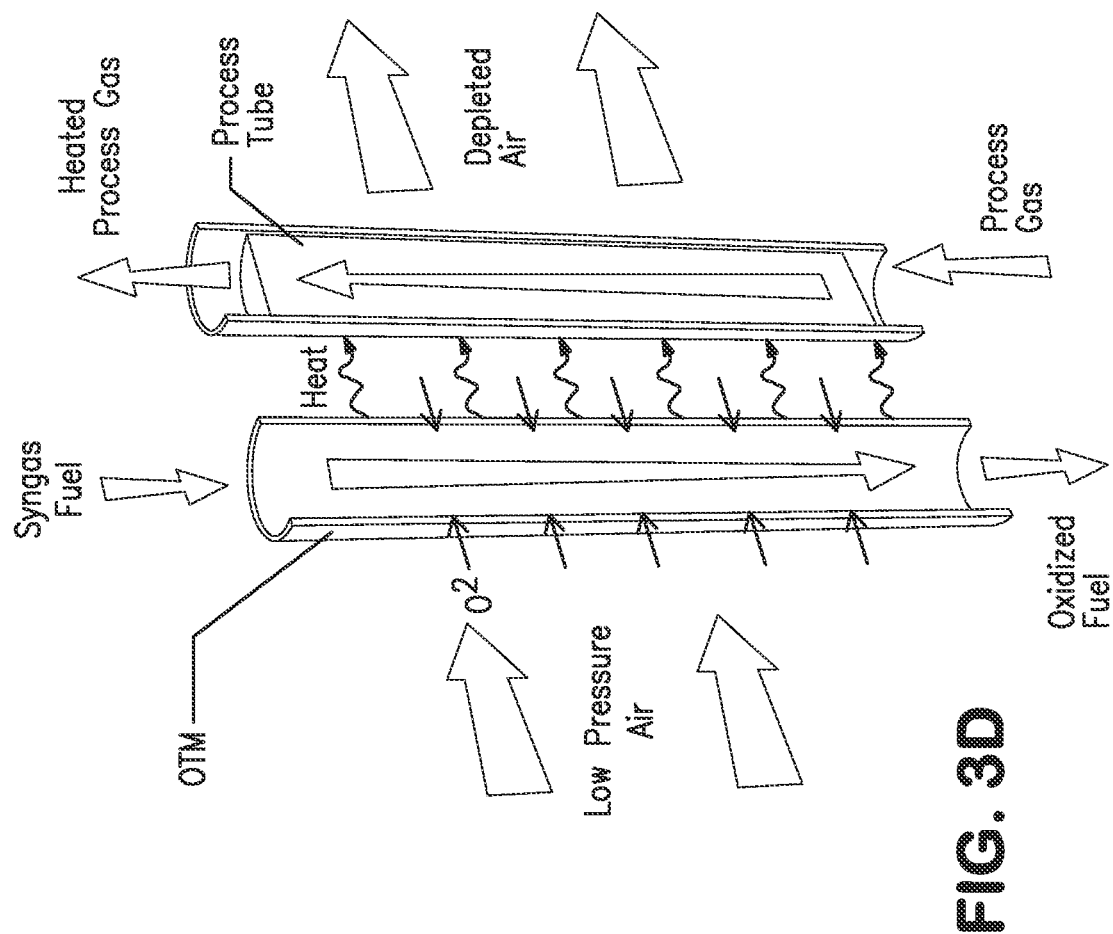
Figure 20:
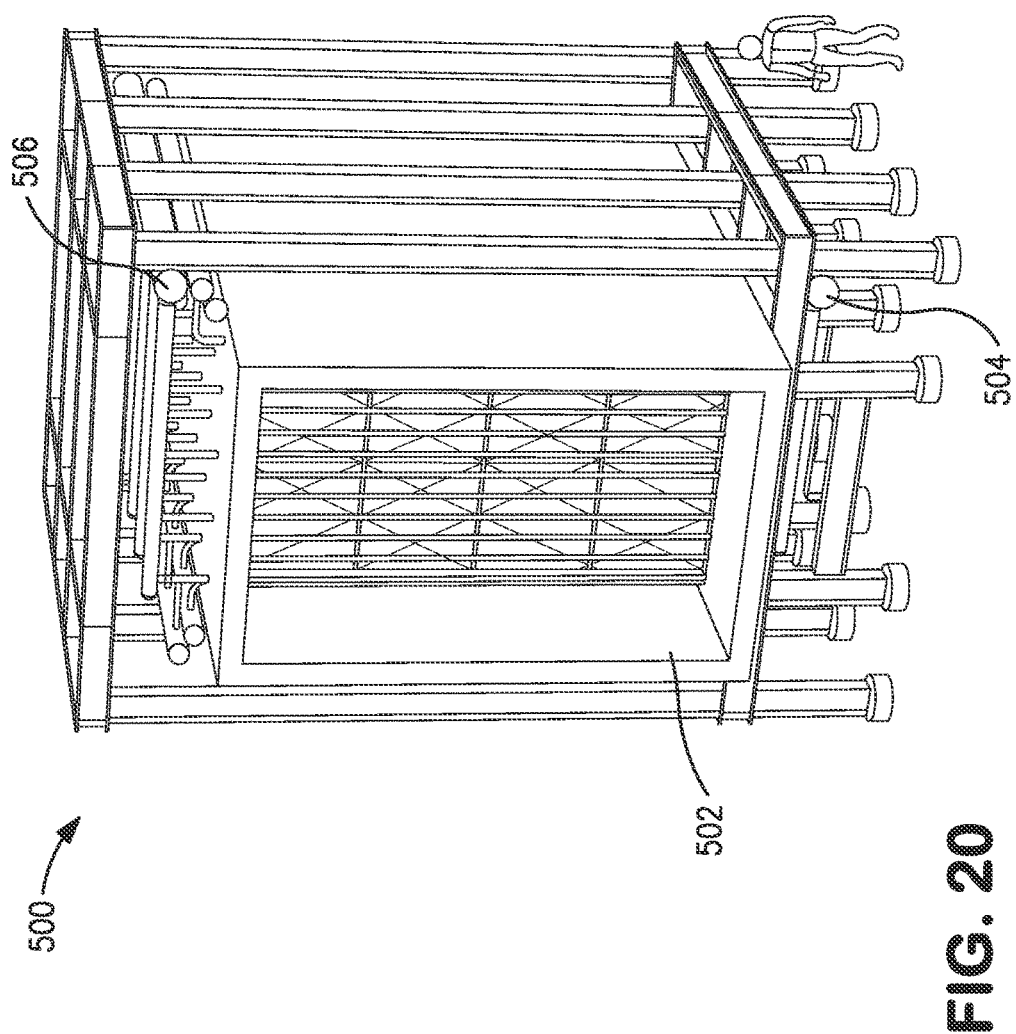
FIG. 20 is a schematic illustration of a an oxygen transport membrane based steam generator or an oxygen transport membrane based process gas heater.
Figure 21:
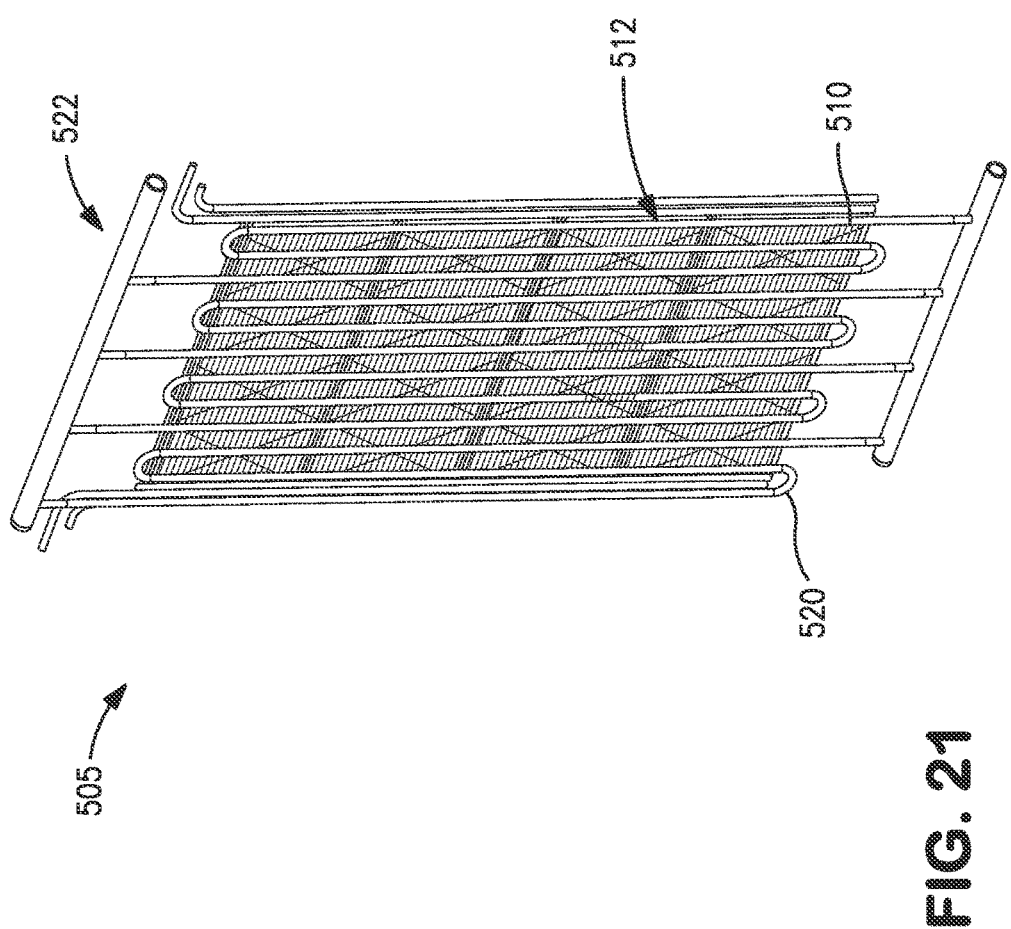
FIG. 21 is a schematic illustration of an integrated dual panel module or panel array for an oxygen transport membrane based steam generator or an oxygen transport membrane based process gas heater.

FIGS. 3C, 3D show a high-level schematic illustration of an oxygen transport membrane based boiler or process gas heater, More specifically, FIGS. 20 and 21 shown a conceptual design for a 50 kW fired-duty oxygen transport membrane based boiler or process gas heater 500 in which a panel array type arrangement of oxygen transport membranes tubes 510 and steam or process gas tubes 520 similar to that described above with reference to the oxygen transport membrane based reforming reactor are used. The oxygen transport membrane boiler or process gas heater 500 is preferably arranged in a modular fashion integrating a plurality of oxygen transport membrane panels 512 and adjacent steam generator or gas panels 522. The illustrated oxygen transport membrane panels 512 and steam/process gas panels 522 are arranged generally in a parallel orientation (although non-parallel arrangements can be employed). The panels can be increased in size or quantity to accommodate larger systems and capacities. A plurality of the integrated panels or arrays 505 are preferably housed in an insulated hot-air duct 502 with a common feed water drum or manifold 504 arranged in a cooler zone outside the hot air duct and a common steam drum or manifold 506 also arranged in a separate zone. Process gas connections are preferably arranged on the top or one side of the boiler or heater 500, making the other side accessible for maintenance.

The integrated packing arrangement of oxygen transport membrane tubes and steam/process gas tubes provides for efficient heat transfer, primarily through radiation of heat from the oxygen transport membrane tubes to the steam/process gas tubes. This arrangement also provides an oxygen transport membrane based boiler reactor or other gas heating reactor to have similar advantages as the above-described oxygen transport membrane based reforming reactor with respect to packing density, modularization, low cost manufacturing, shop-fab modules, and scalability.

While the invention herein disclosed has been described by means of specific embodiments and processes associated therewith, numerous modifications and variations can be made thereto by those skilled in the art without departing from the scope of the invention as set forth in the claims or sacrificing all its material advantages.

What is claimed is:

1. A method for temperature control in a multi-stage reactively driven oxygen transport membrane based reactor comprising the steps of:
    introducing a flow of a heated oxygen containing feed stream to the multi-stage reactively driven oxygen transport membrane based reactor, the heated oxygen containing feed stream having a temperature from about 800° C. to about 1000° C.;
    passing the heated oxygen containing feed stream across the surfaces of a plurality of oxygen transport membrane elements in a first stage of the multi-stage reactively driven oxygen transport membrane based reactor wherein the some oxygen is depleted from the heated oxygen containing feed stream to produce a first residual stream at a temperature at or above the heated oxygen containing feed stream temperature;
    passing the first residual stream through a first refractory air diffusion screen disposed proximate a distal end of the first stage of the multi-stage reactively driven oxygen transport membrane based reactor and configured to maintain an operating temperature in the first stage of the multi-stage reactively driven oxygen transport membrane based reactor and allow the first residual stream to pass therethrough;
    passing the first residual stream across the surfaces of a second plurality of oxygen transport membrane elements in a second stage of the multi-stage reactively driven oxygen transport membrane based reactor wherein the some oxygen is further depleted from the first residual stream to produce a second residual stream;
    passing the second residual stream through a second refractory air diffusion screen disposed proximate a distal end of the second stage of the multi-stage reactively driven oxygen transport membrane based reactor and configured to maintain an operating temperature in the second stage of the multi-stage reactively driven oxygen transport membrane based reactor and allow the second residual stream to pass therethrough; and
    exhausting a stream containing some or all of the second residual stream from the multi-stage reactively driven oxygen transport membrane based reactor;
    wherein the operating temperature in the first stage and the operating temperature in the second stage are within about 25° C. of each other.

2. The method for air temperature control as set forth in claim 1 wherein the temperature of the first residual stream and the temperature of the second residual stream are within about 25° C. of each other.

3. The method for air temperature control as set forth in claim 1 further comprising the step of adding a supplemental oxygen containing stream to the first residual stream wherein the temperature of the first residual stream is not greater than about 50° C. above the heated oxygen containing feed stream.

4. The method for air temperature control as set forth in claim 3 wherein the temperature of the exhausted stream is not greater than about 50° C. above the heated oxygen containing feed stream.

5. The method for air temperature control as set forth in claim 3 wherein the temperature of the second residual stream is not greater than about 50° C. above the heated oxygen containing feed stream.

6. The method for air temperature control as set forth in claim 1 wherein the multi-stage reactively driven oxygen transport membrane based reactor is a reactively driven oxygen transport membrane based reforming reactor.

7. The method for air temperature control as set forth in claim 1 wherein the multi-stage reactively driven oxygen transport membrane based reactor is a reactively driven oxygen transport membrane boiler.

8. The method for air temperature control as set forth in claim 1 wherein the multi-stage reactively driven oxygen transport membrane based reactor is a reactively driven oxygen transport membrane based process gas heater.

9. A method for temperature control in a multi-stage reactively driven oxygen transport membrane based reactor comprising the steps of:
    introducing a flow of a heated oxygen containing feed stream to the multi-stage reactively driven oxygen transport membrane based reactor, the heated oxygen containing feed stream having a temperature from about 800° C. to about 1000° C.;
    passing the heated oxygen containing feed stream across the surfaces of a plurality of oxygen transport membrane elements in a first stage of the multi-stage reactively driven oxygen transport membrane based reactor wherein the some oxygen is depleted from the heated oxygen containing feed stream to produce a first residual stream at a temperature at or above the heated oxygen containing feed stream temperature;
    passing the first residual stream through a first refractory air diffusion screen disposed proximate a distal end of the first stage of the multi-stage reactively driven oxygen transport membrane based reactor and configured to maintain an operating temperature in the first stage of the multi-stage reactively driven oxygen transport membrane based reactor and allow the first residual stream to pass therethrough;
    introducing a flow of supplemental cooling air to the first residual stream at a location downstream of the first refractory air diffusion screen within the multi-stage oxygen transport membrane based reactor
    mixing the flow of supplemental cooling air with the first residual stream to produce a mixed stream having a mixed stream temperature;

passing the mixed stream across the surfaces of a second plurality of oxygen transport membrane elements in a second stage of the multi-stage reactively driven oxygen transport membrane based reactor wherein the some oxygen is depleted from the mixed stream to produce a second residual stream at a temperature above the mixed stream temperature;

passing the second residual stream through a second refractory air diffusion screen disposed proximate a distal end of the second stage of the multi-stage reactively driven oxygen transport membrane based reactor and configured to maintain an operating temperature in the second stage of the multi-stage reactively driven oxygen transport membrane based reactor and allow the second residual stream to pass therethrough; and exhausting a stream containing some or all of the second residual stream from the multi-stage reactively driven oxygen transport membrane based reactor;

wherein the operating temperature in the first stage and the operating temperature in the second stage are within about 25° C. of each other.

10. The method for air temperature control as set forth in claim 9 wherein the temperature of the first residual stream and the temperature of the second residual stream are within about 25° C. of each other.

11. The method for air temperature control as set forth in claim 9 wherein the temperature of the exhausted stream is not greater than about 50° C. above the heated oxygen containing feed stream.

12. The method for air temperature control as set forth in claim 9 wherein the temperature of the first residual stream is not greater than about 50° C. above the heated oxygen containing feed stream.

13. The method for air temperature control as set forth in claim 9 wherein the temperature of the second residual stream is not greater than about 50° C. above the heated oxygen containing feed stream.

14. The method for air temperature control as set forth in claim 9 wherein the temperature of the second residual stream is not greater than about 50° C. above the mixed stream temperature.

15. The method for air temperature control as set forth in claim 9 wherein the multi-stage reactively driven oxygen transport membrane based reactor is a reactively driven oxygen transport membrane based reforming reactor.

16. The method for air temperature control as set forth in claim 9 wherein the multi-stage reactively driven oxygen transport membrane based reactor is a reactively driven oxygen transport membrane boiler.

17. The method for air temperature control as set forth in claim 9 wherein the multi-stage reactively driven oxygen transport membrane based reactor is a reactively driven oxygen transport membrane based process gas heater.

* * * * *